United States Patent [19]
Breslow et al.

[11] Patent Number: 6,087,367
[45] Date of Patent: *Jul. 11, 2000

[54] POTENT INDUCERS OF TERMINAL DIFFERENTIATION AND METHODS OF USE THEREOF

[75] Inventors: Ronald Breslow, Englewood, N.J.; Paul A. Marks, Bridgewater, Conn.; Richard A. Rifkind, New York, N.Y.; Branko Jursic, New Orleans, La.

[73] Assignees: Sloan-Kettering Institute for Cancer Research; The Trustees of Columbia University in the City of New York, both of New York, N.Y.

[ * ] Notice: This patent is subject to a terminal disclaimer.

[21] Appl. No.: 09/314,195

[22] Filed: May 18, 1999

Related U.S. Application Data

[60] Continuation of application No. 08/222,685, Apr. 4, 1994, which is a division of application No. 07/771,760, Oct. 4, 1991, Pat. No. 5,369,108.

[51] Int. Cl.[7] .......................... A01N 43/90; A01N 43/40; A01N 37/18
[52] U.S. Cl. .......................... 514/266; 514/316; 514/330; 514/352; 514/371; 514/616
[58] Field of Search .................................. 514/266, 316, 514/330, 352, 371, 616

[56] References Cited

U.S. PATENT DOCUMENTS

| | | | |
|---|---|---|---|
| 2,279,560 | 4/1942 | Dietrich | 252/47 |
| 2,279,973 | 4/1942 | Dietrich | 252/51 |
| 2,346,665 | 4/1944 | Cupery | 200/500 |
| 2,895,991 | 7/1959 | Randall | 260/558 |
| 3,450,673 | 6/1969 | McKillip | 260/75 |
| 3,632,783 | 1/1972 | Stonis | 424/320 |
| 3,875,301 | 4/1975 | Windheuser | 424/45 |
| 4,056,524 | 11/1977 | Walker | 71/92 |
| 4,442,305 | 4/1984 | Weitl et al. . | |
| 4,480,125 | 10/1984 | Haas et al. | 562/457 |
| 4,537,781 | 8/1985 | Darling | 564/144 |
| 4,611,053 | 9/1986 | Sasa | 528/335 |
| 4,614,815 | 9/1986 | Cognigni et al. | 560/88 |
| 4,801,748 | 1/1989 | Murahashi et al. | 564/126 |
| 4,863,967 | 9/1989 | Hall et al. | 514/615 |
| 4,882,346 | 11/1989 | Driscoll et al. | 514/389 |
| 5,055,608 | 10/1991 | Marks et al. | 560/169 |
| 5,175,191 | 12/1992 | Marks et al. | 514/616 |
| 5,330,744 | 7/1994 | Pontremoli et al. | 424/10 |

FOREIGN PATENT DOCUMENTS

| | | |
|---|---|---|
| 0119428 | of 0000 | European Pat. Off. . |
| 0433662 | of 0000 | European Pat. Off. . |
| 0576941 | of 0000 | European Pat. Off. . |
| 3505250 | of 0000 | Germany . |

OTHER PUBLICATIONS

Marks et al., *Proc. Natl. Acad. Sci.*, vol. 86, pp. 6358–6362 (Aug. 1989).
Chun et al., *Cancer Treatment Reports*, vol. 70, pp. 991–996 (Aug. 1986).
Reuben et al., *J. Biolog. Chem.*, vol. 253, pp. 4214–4218 (Jun. 1978).
Tanaka et al., *Proc. Natl. Acad. Sci.* (USA), vol. 72, pp. 1003–1006 (Mar. 1975).
Fibach et al., *Cancer Research*, vol. 37, pp. 440–444 (Feb. 1977).
Melloni et al., *Chem. Abs.*, vol. 109, No. 47737e (1988).
Hozumi et al., *Int. J. Cancer*, vol. 23, pp. 119–122 (1979).
Haces et al., *J. Med. Chem.*, vol. 30, pp. 405–409 (1987).
Das et al., *Chem. Abs.*, vol. 101, No. 54665t (1984).
Brown et al., *Chem. Abs.*, vol. 105, No. 7850lv (1986).
Hynes, *J. Med. Chem.*, vol. 13, No. 6, pp. 1235–1237 (1971).
Tabernero et al., *Chem. Abs.*, vol. 98, No. 191329v (1983).
Morrison and Boyd, *Organic Chemistry* (3rd ed. Allyn and Bacon Boston) (1973) p. 755.
Weitl et al., *J. Org. Chem.*, vol. 46, pp. 5234–5237 (1981).
Breslow et al., *Proc. Natl. Acad. Sci. USA*, vol. 88, pp. 5542–5546 (1991).
Brown, *American Chemical Society* 3729–3796.
Chugai Phasmaceutical Co., Ltd. *Chem. Abs.* vol. 101, No. 124925d (1984).
Mueller et al., *Chem. Abs.*, vol. 103, No. 192908s (1985).
Prabhakar, et al., Birla Institute of Technology and Science, pp. 1030–1033.

*Primary Examiner*—John Kight
*Assistant Examiner*—Raymond Covington
*Attorney, Agent, or Firm*—John P. White; Cooper & Dunham LLP

[57] ABSTRACT

The present invention provides the compound having the structure:

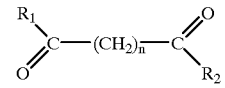

wherein each of $R_1$ and $R_2$ are independently the same as or different from each other; when $R_1$ and $R_2$ are the same, each is a substituted or unsubstituted arylamino, cycloalkylamino, pyridineamino, piperidino, 9-purine-6-amine, or thiozoleamino group; when $R_1$ and $R_2$ are different, $R_1=R_3$—N—$R_4$, wherein each of $R_3$ and $R_4$ are independently the same as or different from each other and are a hydrogen atom, a hydroxyl group, a substituted or unsubstituted, branched or unbranched alkyl, alkenyl, cycloalkyl, aryl, alkyloxy, aryloxy, arylalkyloxy, or pyridine group, or $R_3$ and $R_4$ bond together to form a piperidine group and $R_2$ is a hydroxylamino, hydroxyl, amino, alkylamino, dialkylamino or alkyloxy group; and n is an integer from about 4 to about 8.

The present invention also provides a method of selectively inducing terminal differentiation of neoplastic cells and thereby inhibiting proliferation of such cells. Moreover, the present invention provides a method of treating a patient having a tumor characterized by proliferation of neoplastic cells. Lastly, the present invention provides a pharmaceutical composition comprising a pharmaceutically acceptable carrier and a therapeutically acceptable amount of the compound above.

19 Claims, No Drawings

POTENT INDUCERS OF TERMINAL DIFFERENTIATION AND METHODS OF USE THEREOF

This is a continuation of U.S. Ser. No. 08/222,685 filed Apr. 4, 1994, now allowed, which is a divisional of U.S. Ser. No. 07/771,760, filed Oct. 4, 1991, now U.S. Pat. No. 5,369,108, issued on Nov. 29, 1994, the contents of all of which are hereby incorporated by reference.

BACKGROUND OF THE INVENTION

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

Cancer is a disorder in which a population of cells has become, in varying degrees, unresponsive to the control mechanisms which normally govern proliferation and differentiation. For many years there have been two principal strategies for chemotherapeutic treatment of cancer: a) blocking hormone-dependent tumor cell proliferation by interference with the production or peripheral action of sex hormones; and b) killing cancer cells directly by exposing them to cytotoxic substances, which injure both neoplastic and normal cell populations.

Relatively recently, cancer therapy is also being attempted by the induction of terminal differentiation of the neoplastic cells (1). In cell culture models differentiation has been reported by exposure of cells to a variety of stimuli, including: cyclic AMP and retinoic acid (2,3), aclarubicin and other anthracyclines (4).

There is abundant evidence that neoplastic transformation does not necessarily destroy the potential of cancer cells to differentiate (1,5,6). There are many examples of tumor cells which do not respond to the normal regulators of proliferation and appear to be blocked in the expression of their differentiation program, and yet can be induced to differentiate and cease replicating. A variety of agents, including some relatively simple polar compounds (5,7–9), derivatives of vitamin D and retinoic acid (10–12), steroid hormones (13), growth factors (6,14), proteases (15,16), tumor promoters (17,18), and inhibitors of DNA or RNA synthesis (4,19–24), can induce various transformed cell lines and primary human tumor explants to express more differentiated characteristics.

Early studies by the present inventors identified a series of polar compounds that were effective inducers of differentiation in a number of transformed cell lines (8,9). of these, the most effective inducer, was the hybrid polar/apolar compound N,N'-hexamethylene bisacetamide (HMBA) (9). The use of this polar/apolar compound to induce murine erythroleukemia cells (MELC) to undergo erythroid differentiation with suppression of oncogenicity has proved a useful model to study inducer-mediated differentiation of transformed cells (5,7–9). HMBA-induced MELC terminal erythroid differentiation is a multistep process. Upon addition of HMBA to MELC (745A-DS19) in culture, there is a latent period of 10 to 12 hours before commitment to terminal differentiation is detected. Commitment is defined as the capacity of cells to express terminal differentiation despite removal of inducer (25). Upon continued exposure to HMBA there is progressive recruitment of cells to differentiate. The present inventors have reported that MELC cell lines made resistant to relatively low levels of vincristine become markedly more sensitive to the inducing action of HMBA and can be induced to differentiate with little or no latent period (26).

HMBA is capable of inducing phenotypic changes consistent with differentiation in a broad variety of cells lines (5). The characteristics of the drug induced effect have been most extensively studied in the murine erythroleukemia cell system (MELC) (5,25,27,28). MELC induction of differentiation is both time and concentration dependent. The minimum concentration required to demonstrate an effect in vitro in most strains is 2 to 3 mM; the minimum duration of continuous exposure generally required to induce differentiation in a substantial portion (>20%) of the population without continuing drug exposure is about 36 hours.

The primary target of action of HMBA is not known. There is evidence that protein kinase C is involved in the pathway of inducer-mediated differentiation (29). The in vitro studies provided a basis for evaluating the potential of HMBA as a cytodifferentiation agent in the treatment of human cancers (30). S several phase I clinical trials with HMBA have been completed (31–36). Clinical trials have shown that this compound can induce a therapeutic response in patients with cancer (35,36). However, these phase I clinical trials also have demonstrated that the potential efficacy of HMBA is limited, in part, by dose-related toxicity which prevents achieving optimal blood levels and by the need for intravenous administration of large quantities of the agent, over pro longed periods.

Recently, the present inventors have reported a number of compounds related to HMBA with polar groups separated by apolar linkages that, on a molar basis, are as active (37) or 100 times more active than HMBA (38). As a class, however, it has been found that the symmetrical dimers such as HMBA and related compounds are not the best cytodifferentiating agents.

It has unexpectedly been found that the best compounds comprise two polar end groups separated by a flexible chain group. These compounds are unexpectedly a thousand times more active than HMBA and ten times more active than HMBA related compounds.

This new class of compounds of the present invention may be useful for selectively inducing terminal differentiation of neoplastic cells and therefore aid in treatment of tumors in patients.

SUMMARY OF THE INVENTION

The present invention provides the compound having the structure:

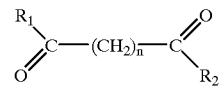

wherein each of $R_1$ and $R_2$ are independently the same as or different from each other; when $R_1$ and $R_2$ are the same, each is a substituted or unsubstituted arylamino, cycloalkylamino, pyridineamino, piperidino, 9-purine-6-amine, or thiozoleamino group; when $R_1$ and $R_2$ are different, $R_1=R_3$—N—$R_4$, wherein each of $R_3$ and $R_4$ are independently the same as or different from each other and are a hydrogen atom, a hydroxyl group, a substituted or unsubstituted, branched or unbranched alkyl, alkenyl, cycloalkyl, aryl, alkyloxy, aryloxy, arylalkyloxy, or pyridine group, or $R_3$ and $R_4$ bond together to form a piperidine group and $R_2$ is a hydroxylamino, hydroxyl, amino, alkylamino, dialkylamino or alkyloxy group; and n is an integer from about 4 to about 8.

The present invention also provides the compound above having the structure:

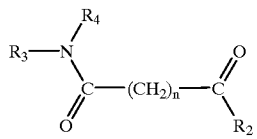

wherein each of $R_3$ and $R_4$ are independently the same as or different from each other and are a hydrogen atom, a hydroxyl group, a substituted or unsubstituted, branched or unbranched alkyl, alkenyl, cycloalkyl, aryl, alkyloxy, aryloxy, arylalkyloxy, or pyridine group, or $R_3$ and $R_4$ bond together to form a piperidine group; $R_2$ is a hydroxylamino, hydroxyl, amino, alkylamino, dialkylamino or alkyloxy group; and n is an integer from about 4 to about 8.

The present invention also provides the compound above having the structure:

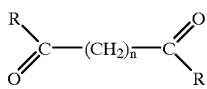

wherein R is a substituted or unsubstituted arylamino, cycloalkylamino, pyridineamino, piperidino, 9-purine-6-amine, or thiozoleamino group; and n is an integer from about 4 to about 8.

The present invention also provides the compound having the structure:

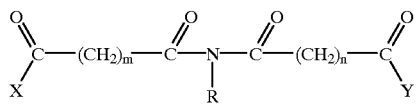

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; R is a hydrogen atom, a hydroxyl group, a substituted or unsubstituted alkyl, aryl, alkyloxy, or aryloxy group; and each of m and n are independently the same as or different from each other and are each an integer from about 0 to about 8.

The present invention further provides the compound having the structure:

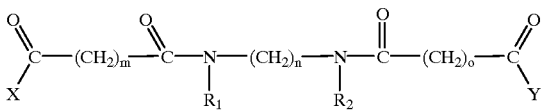

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; each of $R_1$ and $R_2$ are independently the same as or different from each other and are a hydrogen atom, a hydroxyl group, a substituted or unsubstituted alkyl, aryl, alkyloxy, or aryloxy group; and each of m, n, and o are independently the same as or different from each other and are each an integer from about 0 to about 8.

The present invention still further provides the compound having the structure:

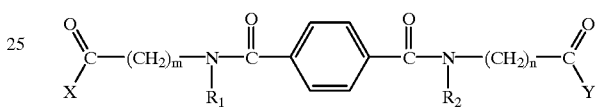

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; each of $R_1$ and $R_2$ are independently the same as or different from each other and are a hydrogen atom, a hydroxyl group, a substituted or unsubstituted alkyl, aryl, alkyloxy, or aryloxy group; and each of m and n are independently the same as or different from each other and are each an integer from about 0 to about 8.

The present invention also provides the compound having the structure:

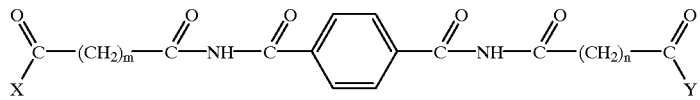

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; and each of m and n are independently the same as or different from each other and are each an integer from about 0 to about 8.

The present invention also provides the compound having the structure:

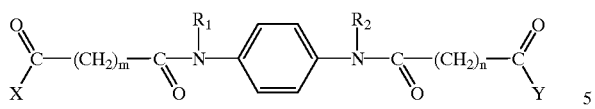

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; each of $R_1$ and $R_2$ are independently the same as or different from each other and are a hydrogen atom, a hydroxyl group, a substituted or unsubstituted alkyl, aryl, alkyloxy, or aryloxy group; and each of m and n are independently the same as or different from each other and are each an integer from about 0 to about 8.

The present invention further provides the compound having the structure:

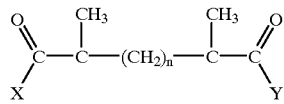

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; and n is an integer from about 0 to about 8.

The present invention still further provides the compound having the structure:

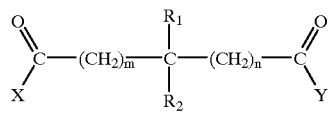

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; each of $R_1$ and $R_2$ are independently the same as or different from each other and are a hydrogen atom, a hydroxyl group, a substituted or unsubstituted alkyl, aryl, alkyloxy, aryloxy, carbonylhydroxylamino, or fluoro group; and each of m and n are independently the same as or different from each other and are each an integer from about 0 to about 8.

The present invention also provides the compound having the structure:

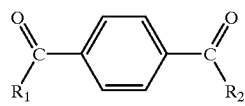

wherein each of $R_1$ and $R_2$ are independently the same as or different from each other and are a hydroxyl, alkyloxy, amino, hydroxylamino, alkylamino, dialkylamino, arylamino, alkylarylamino, alkyloxyamino, aryloxyamino, alkyloxyalkylamino, or aryloxyalkylamino group.

The present invention also provides the compound having the structure:

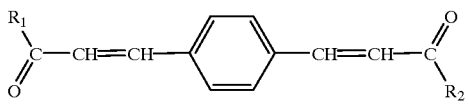

wherein each of $R_1$ and $R_2$ are independently the same as or different from each other and are a hydroxyl, alkyloxy, amino, hydroxylamino, alkylamino, dialkylamino, arylamino, alkylarylamino, alkyloxyamino, aryloxyamino, alkyloxyalkylamino, or aryloxyalkylamino group.

The present invention further provides the compound having the structure:

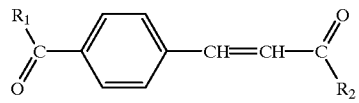

wherein each of $R_1$ and $R_2$ are independently the same as or different from each other and are a hydroxyl, alkyloxy, amino, hydroxylamino, alkylamino, dialkylamino, arylamino, alkylarylamino, alkyloxyamino, aryloxyamino, alkyloxyalkylamino, or aryloxyalkylamino group.

In addition, the present invention provides a method of selectively inducing terminal differentiation of neoplastic cells and thereby inhibiting proliferation of such cells which comprises contacting the cells under suitable conditions with an effective amount of any of the compounds above, effective to selectively induce terminal differentiation.

The present invention also provides a method of treating a patient having a tumor characterized by proliferation of neoplastic cells which comprises administering to the patient an effective amount of any of the compounds above, effective to selectively induce terminal differentiation of such neoplastic cells and thereby inhibit their proliferation.

Lastly, the present invention provides a pharmaceutical composition comprising a pharmaceutically acceptable carrier and a therapeutically acceptable amount of any of the compounds above.

DETAILED DESCRIPTION OF THE INVENTION

The present invention provides the compound having the structure:

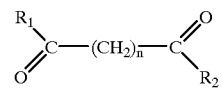

wherein each of $R_1$ and $R_2$ are independently the same as or different from each other; when $R_1$ and $R_2$ are the same, each is a substituted or unsubstituted arylamino, cycloalkylamino, pyridineamino, piperidino, 9-purine-6-amine, or thiozoleamino group; when $R_1$ and $R_2$ are different, $R_1=R_3-N-R_4$, wherein each of $R_3$ and $R_4$ are independently the same as or different from each other and are a hydrogen atom, a hydroxyl group, a substituted or unsubstituted, branched or unbranched alkyl, alkenyl, cycloalkyl, aryl, alkyloxy, aryloxy, arylalkyloxy, or pyridino group, or $R_3$ and $R_4$ bond together to form a piperidine group and $R_2$ is a hydroxylamino, hydroxyl, amino, alkylamino, dialkylamino or alkyloxy group; and n is an integer from about 4 to about 8.

The present invention also provides the compound above having the structure:

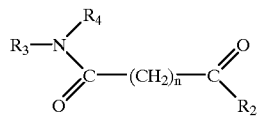

wherein each of $R_3$ and $R_4$ are independently the same as or different from each other and are a hydrogen atom, a hydroxyl group, a substituted or unsubstituted, branched or unbranched alkyl, alkenyl, cycloalkyl, aryl, alkyloxy, aryloxy, arylalkyloxy, or pyridine group, or $R_3$ and $R_4$ bond together to form a piperidine group; $R_2$ is a hydroxylamino, hydroxyl, amino, alkylamino, dialkylamino or alkyloxy group; and n is an integer from about 4 to about 8.

In the preferred embodiment of the compound above, $R_2$ is a hydroxylamino, hydroxyl, amino, methylamino, dimethylamino, or methyoxy group and n is 6. Most preferably, $R_4$ is a hydrogen atom and $R_3$ is a substituted or unsubstituted phenyl group.

The phenyl group may be substituted with a methyl, cyano, nitro, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methyoxy, benzyloxy, phenylaminooxy, phenylmethoxy, phenylaminocarbonyl, methyoxycarbonyl, methylaminocarbonyl, dimethylamino, dimethylaminocarbonyl, or hydroxylaminocarbonyl group.

In other preferred embodiments of the compound above, $R_4$ is a hydrogen atom and $R_3$ is a cyclohexyl group; $R_4$ is a hydrogen atom and $R_3$ is a methyoxy group; $R_3$ and $R_4$ each bond together to form a piperidine group; $R_4$ is a hydrogen atom and $R_3$ is a hydroxyl group; $R_4$ is a hydrogen atom and $R_3$ is a benzyloxy group; $R_4$ is a hydrogen atom and $R_3$ is a δ-pyridine group; $R_4$ is a hydrogen atom and $R_3$ is a β-pyridine group; $R_4$ is a hydrogen atom and $R_3$ is a α-pyridine group; $R_3$ and $R_4$ are both methyl groups; or $R_4$ is a methyl group and $R_3$ is a phenyl group.

The present invention also provides the compound having the structure:

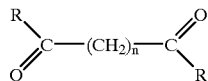

wherein R is a substituted or unsubstituted arylamino, cycloalkylamino, pyridineamino, piperidino, 9-purine-6-amine, or thiozoleamino group; and n is an integer from about 4 to about 8.

In the preferred embodiment of the compound above, R is a substituted or unsubstituted phenylamino group. The phenylamino group may be substituted with a cyano, methylcyano, nitro, carboxyl, aminocarbonyl, methylaminocarbonyl, dimethylaminocarbonyl, trifluoromethyl, hydroxylaminocarbonyl, N-hydroxylaminocarbonyl, methoxycarbonyl, chloro, fluoro, methyl, methoxy, 2,3-difluoro, 2,3-difluoro, 2,4-difluoro, 2,5-difluoro, 2,6-difluoro, 3,5-difluoro, 2,6-difluoro, 2,3,6-trifluoro, 1,2,3-trifluoro, 3,4,5-trifluoro, 2,3,4,5-tetrafluoro, or 2,3,4,5,6-pentafluoro group.

In another embodiment of the compound above, R is a cyclohexylamino group.

The present invention also provides the compound having the structure:

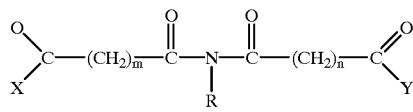

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; R is a hydrogen atom, a hydroxyl group, a substituted or unsubstituted alkyl, aryl, alkyloxy, or aryloxy group; and each of m and n are independently the same as or different from each other and are each an integer from about 0 to about 8.

In the preferred embodiment of the compound above, each of X, Y, and R is a hydroxyl group and each of m and n is 5.

The present invention also provides the compound having the structure:

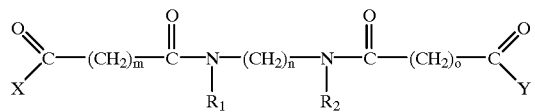

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; each of $R_1$ and $R_2$ are independently the same as or different from each other and are a hydrogen atom, a hydroxyl group, a substituted or unsubstituted alkyl, aryl, alkyloxy, or aryloxy group; and each of m, n, and o are independently the same as or different from each other and are each an integer from about 0 to about 8.

In the preferred embodiment of the compound above, each of X and Y is a hydroxyl group and each of $R_1$ and $R_2$ is a methyl group. Most preferably, each of n and o is 6, and m is 2.

The present invention also provides the compound having the structure:

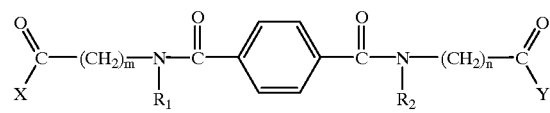

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; each of $R_1$ and $R_2$ are independently the same as or different from each other and are a hydrogen atom, a hydroxyl group, a substituted or unsubstituted alkyl, aryl, alkyloxy, or aryloxy group; and each of m and n are independently the same as or different from each other and are each an integer from about 0 to about 8.

The present invention also provides the compound having the structure:

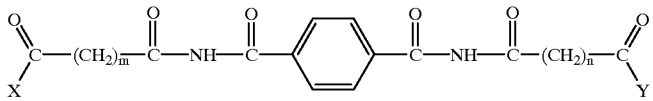

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; and each of m and n are independently the same as or different from each other and are each an integer from about 0 to about 8.

In the preferred embodiment of the compound above, each of X and Y is a hydroxyl group and each of m and n is 5.

The present invention also provides the compound having the structure:

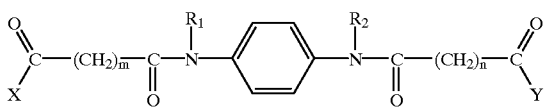

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; each of $R_1$ and $R_2$ are independently the same as or different from each other and are a hydrogen atom, a hydroxyl group, a substituted or unsubstituted alkyl, aryl, alkyloxy, or aryloxy group; and each of m and n are independently the same as or different from each other and are each an integer from about 0 to about 8.

The present invention also provides the compound having the structure:

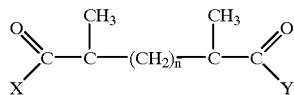

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; and n is an integer from about 0 to about 8.

In the preferred embodiment of the compound above, each of X and Y is a dimethylamino group and n is 4 or 5.

The present invention also provides the compound having the structure:

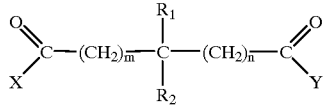

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; each of $R_1$ and $R_2$ are independently the same as or different from each other and are a hydrogen atom, a hydroxyl group, a substituted or unsubstituted alkyl, aryl, alkyloxy, aryloxy, carbonylhydroxylamino, or fluoro group; and each of m and n are independently the same as or different from each other and are each an integer from about 0 to about 8.

In the preferred embodiment of the compound above, each of X and Y is a hydroxylamino group, $R_1$ is a methyl group, $R_2$ is a hydrogen atom, and each of m and n is 2. In another preferred embodiment, each of X and Y is a hydroxylamino group, $R_1$ is a carbonylhydroxylamino group, $R_2$ is a hydrogen atom, and each of m and n is 5. In a further preferred embodiment, each of X and Y is a hydroxylamino group, each of $R_1$ and $R_2$ is a fluoro group, and each of m and n is 2.

The present invention also provides the compound having the structure:

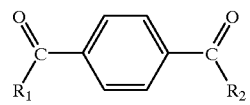

wherein each of $R_1$ and $R_2$ are independently the same as or different from each other and are a hydroxyl, alkyloxy, amino, hydroxylamino, alkylamino, dialkylamino, arylamino, alkylarylamino, alkyloxyamino, aryloxyamino, alkyloxyalkylamino, or aryloxyalkylamino group.

Preferably, $R_1$ is a phenylamino group and $R_2$ is a hydroxylamino group.

The present invention also provides the compound having the structure:

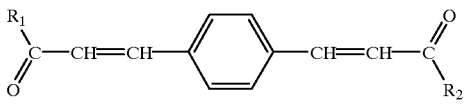

wherein each of $R_1$ and $R_2$ are independently the same as or different from each other and are a hydroxyl, alkyloxy, amino, hydroxylamino, alkylamino, dialkylamino, arylamino, alkylarylamino, alkyloxyamino, aryloxyamino, alkyloxyalkylamino, or aryloxyalkylamino group.

Preferably, $R_1$ is phenylamino group and $R_2$ is hydroxylamino group.

The present invention also provides the compound having the structure:

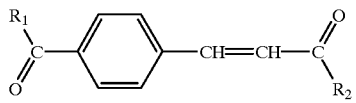

wherein each of $R_1$ and $R_2$ are independently the same as or different from each other and are a hydroxyl, alkyloxy, amino, hydroxylamino, alkylamino, dialkylamino, arylamino, alkylarylamino, alkyloxyamino, aryloxyamino, alkyloxyalkylamino, or aryloxyalkylamino group.

In the preferred embodiment, either $R_1$ or $R_2$ is a hydroxylamino group.

The present invention also provides a method of selectively inducing terminal differentiation of neoplastic cells and thereby inhibiting proliferation of such cells which comprises contacting the cells under suitable conditions with an effective amount of any of the compounds above, effective to selectively induce terminal differentiation.

The contacting must be performed continuously for a prolonged period of time, i.e. for at least 48 hours, preferably for about 4–5 days or longer.

The method may be practiced in vivo or in vitro. If the method is practiced in vitro, contacting may be effected by incubating the cells with the compound. The concentration of the compound in contact with the cells should be from about 1 $\mu$M to about 25 mM, preferably from 4 $\mu$M to about 5 mM. The concentration depends upon the individual compound and the state of the neoplastic cells.

The method may also comprise initially treating the cells with an antitumor agent so as to render them resistant to an antitumor agent and subsequently contacting the resulting resistant cells under suitable conditions with an effective amount of any of the compounds above, effective to selectively induce terminal differentiation of such cells.

The antitumor agent may be one of numerous chemotherapy agents such as an alkylating agent, an antimetabolite, a hormonal agent, an antibiotic, colchicine, a vinca alkaloid, L-asparaginase, procarbazine, hydroxyurea, mitotane, nitrosoureas or an imidazole carboxamide. Suitable agents are those agents which promote depolarization of tubulin. Preferably the antitumor agent is colchicine or a vinca alkaloid; especially preferred are vinblastine and vincristine. In embodiments where the antitumor agent is vincristine, the cells preferably are treated so that they are resistant to vincristine at a concentration of about 5 mg/ml. The treating of the cells to render them resistant to an antitumor agent may be effected by contacting the cells with the agent for a period of at least 3–5 days. The contacting of the resulting cells with any of the compounds above is performed as described previously.

The present invention also provides a method of treating a patient having a tumor characterized by proliferation of neoplastic cells which comprises administering to the patient an effective amount of any of the compounds above, effective to selectively induce terminal differentiation of such neoplastic cells and thereby inhibit their proliferation.

The method of the present invention is intended for the treatment of human patients with tumors. However, it is also likely that the method would be effective in the treatment of tumors in other mammals. The term tumor is intended to include any cancer caused by the proliferation of neoplastic cells, such as lung cancer, acute lymphoid myeloma, bladder melanoma, renal carcinoma, breast carcinoma, or colorectal carcinoma. The administration of the compound to the patient may be effected orally or parenterally. To date, administration intravenously has proven to be effective. The administration of the compound must be performed continuously for a prolonged period of time, such as for at least 3 days and preferably more than 5 days. In the most preferred embodiments, the administration is effected continuously for at least 10 days and is repeated at intervals wherein at each interval the administration is continuously effected for at least 10 days. For example, the administration may be effected at intervals as short as 5–10 days, up to about 25–35 days and continuously for at least 10 days during each such interval. The optimal interval period will vary depending on the type of patient and tumor. For example, in the incidence of acute leukemia, the so called myelodysplastic syndrome, continuous infusion would seem to be indicated so long as the patient tolerated the drug without toxicity and there was a positive response.

The amount of the compound administered to the patient is less than an amount which would cause toxicity in the patient. In the certain embodiments, the amount of the compound which is administered to the patient is less than the amount which causes a concentration of the compound in the patient's plasma to equal or exceed the toxic level of the compound. Preferably, the concentration of the compound in the patient's plasma is maintained at about 1.0 mM. It has been found with HMBA that administration of the compound in an amount from about 5 gm/m$^2$/day to about 30 gm/m$^2$/day, particularly about 20 gm/m$^2$/day, is effective without producing toxicity in the patient. The optimal amount of the compound which should be administered to the patient in the practice of the present invention will depend on the particular compound used and the type of cancer being treated.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

The method may also comprise initially administering to the patient an amount of an antitumor agent to render the cells resistant to an antitumor agent and subsequently administering to the patient an effective amount of any of the compounds above, effective to selectively induce terminal differentiation of such neoplastic cells and thereby inhibit their proliferation.

The antitumor agent may be one of numerous chemotherapy agents such as an alkylating agent, an antimetabolite, a hormonal agent, an antibiotic, colchicine, a vinca alkaloid, L-asparaginase, procarbazine, hydroxyurea, mitotane, nitrosoureas or an imidazole carboxamide. Suitable agents are those agents which promote depolarization of tubulin. Preferably the antitumor agent is colchicine or a vinca alkaloid; especially preferred are vinblastine and vincristine. In embodiments where the antitumor agent is vincristine, an amount is administered to render the cells are resistant to vincristine at a concentration of about 5 mg/ml. The administration of the agent is performed essentially as described above for the administration of any of the compounds. Preferably, the administration of the agent is for a period of at least 3–5 days. The administration of any of the compounds above is performed as described previously.

The present invention also provides a pharmaceutical composition comprising a pharmaceutically acceptable carrier, such as sterile pyrogen-free water, and a therapeutically acceptable amount of any of the compounds above.

Preferably, the effective amount is an amount effective to selectively induce terminal differentiation of suitable neoplastic cells and less than an amount which causes toxicity in a patient.

Lastly, the present invention provides the pharmaceutical composition above in combination with an antitumor agent. The antitumor agent may be any of the agents previously described.

The invention is illustrated in the Experimental Details section which follows. This section is set forth to aid in an understanding of the invention but is not intended to, and should not be construed to, limit in any way the invention as set forth in the claims which follow thereafter.

Experimental Details

Cells and Materials

MELC 745A-DS19 cells and the variants of MELC derived from this cell line, namely, the vincristine-resistant MELC V3.17 and VCR.C(2)15 cell lines (26), and the dimethylsulfoxide-resistant cell line, DR10 (39), were maintained in alpha minimal essential medium containing 10% fetal calf serum (16). Cell cultures for all experiments were initiated with cells in logarithmic growth phase (day 2 cultured cells) at a density of $10^5$ cells/ml. Inducer compounds were added in the final concentrations indicated below, dissolved in culture medium without fetal calf serum unless otherwise indicated. Cell density and benzidine reactively were determined as described (16).

Commitment to terminal differentiation, characterized by limited cell division (colony size <32 cells) and accumulation of hemoglobin (benzidine reactive colonies) was assayed by a colony cloning assay using 2% methylcellulose as described (25) (see Table 1 for results).

HL-60 human leukemia cells, derived from peripheral blood leukocytes of a patient with acute promyelocytic leukemia (40). Induced differentiation of HL-60 cells assayed by determining the proportion of cells that developed the capacity to reduce nitroblue tetrazolium (NBT) (41) (see Table 2 for results).

Chemistry

The compounds having the structure:

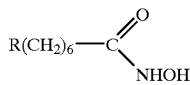

Preparation of $PhCH_2ONHOC(CH_2)_6COOCH_3$:

A solution of suberic acid monomethyl ester (1.9 g; 0.01 mol), oxaloyl chloride (1.75 mL; 2.54 g; 0.02 mol) and 0.1 mL DMF in benzene (200 mL) was stirred overnight at room temperature. The solvent was evaporated and oily residue was dissolved in chloroform (~20 mL) and mixed together with chloroform solution (100 mL) of O-benzylhydroxylamine (2.46 g; 0.02 mol) and pyridine (1.6 mL; 1.68 g; 0.02 mol). The reaction mixture was stirred at room temperature overnight. The chloroform solution was washed with water (50 mL), 10% hydrochloric acid, and again with water (2×50 mL). The organic layer was dried over anhydrous magnesium sulfate and evaporated. The solid residue was slurried in hexanes (~100 mL) and filtered. The yield of $PhCH_2ONHOC(CH_2)_6COOCH_3$ was 2.61 g (89%).

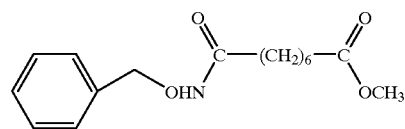

The above suberic acid monobenzyloxyamide monomethyl ester (1 g; 3.4 mol) was dissolved in dry methanol (50 mL) and 5% Pd-C (50 mg) was added. The black suspension was shaken under hydrogen pressure (~50 psi) overnight at room temperature. The catalyst was separated by filtration, and filtrate was evaporated. The solid residue was slurried in hexanes (~20 mL) and filtered. The yield of the monomethyl ester monohydroxamic acid of suberic acid was 900 mg (95%). $^1H$ NMR (DMSO-$d_6$, 200 MHz), $\delta$(ppm) 10.31 (s, NHOH, 1H); 8.89 (s, broad, NHOH, 1H); 3.57 (s, $CH_3$, 3H); 2.27 (t, J=7.4 Hz, $CH_2COOCH_3$, 2H); 1.91 (t, J=7.4 Hz, $CH_2CONHOH$, 2H); 1.49 (m, 4H), 1.24(m, 4H).

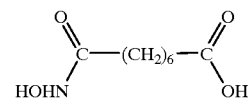

Suberic acid monobenzyloxyamide monomethyl ester (1 g; 3.4 mmol) and potassium hydroxide (210 mg; 3.75 mmol) were dissolved in 10 mL of methanol-water (4:1) mixture. The reaction mixture was refluxed two hours and solvent was evaporated. The solid residue was dissolved in 5 mL water and acidified with conc. hydrochloric acid to pH~5. White precipitate was filtered, dried and crystallized from ethyl acetate-hexanes. The yield of suberic acid monobenzyloxyamide was 820 mg (86%). The product was dissolved in methanol (50 mL) and 5% Pd-C (50 mg) was added. The reaction mixture was shaken under hydrogen pressure (50 psi) overnight. The catalyst was separated by filtration and filtrate was evaporated. The solid residue was slurried in hexanes and filtered. The yield of suberic acid monohydroxamic acid was 520 mg (81%). $^1H$ NMR (DMSO-$d_6$, 200 MHz), $\delta$(ppm) 11.96 (s, broad, COOH, 1H); 10.31 (s, NHOH, 1H); 8.63 (s, broad, NHOH, 1H); 2.17 (s, J=7.4 Hz, $CH_2COOH$, 2H); 1.91 (s, $CH_2CONHOH$, 2H); 1.46 (m, 4H); 1.22 (m, 4H).

Compounds having the structure:

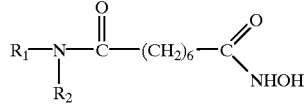

General Procedure

A pyridine (500 mL) solution of O-benzylhydroxylamine (2.46 g; 0.02 mol), the corresponding amine (0.02 mol) and suberoyl chloride was stirred at room temperature overnight. The solvent was evaporated and the semisolid residue was dissolved in 1000 mL chloroform-methanol (4:1); the resulting solution was washed with water (2×100 mL), 10% hydrochloric acid (3×100 mL), and again with water (2×100 mL). Organic layer was dried over anhydrous magnesium sulfate and evaporated. The solid residue was dissolved in methanol (100 mL) and 5% Pd-C was added. The black suspension was shaken under hydrogen pressure (~50 psi) overnight. The catalyst was separated by filtration, and the filtrate was evaporated. The target products were isolated by column chromatography on silica gel with ethyl acetate-tetrahydrofuran.

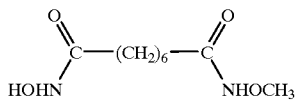

Yield 1.1 g (26%). $^1$H NMR (DMSO-D$_6$, 200 MHz), δ(ppm) 10.93 (s, NHOCH$_3$, 1H); 10.32 (s, NHOH, 1H); 8.66 (s, NHOH, 1H); 3.55 (s, CH$_3$, 3H); 1.91 (t, J=7.6 Hz, CH$_2$CO—, 4H); 1.45 (m, 4H); 1.20 (m, 4H).

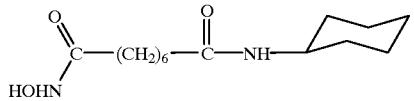

Yield 1.2 g (21%). $^1$H NMR (DMSO-d$_6$, 200 MHz), δ(ppm) 10.31 (s, NHOH, 1H); 8.60 (s, broad, NHOH, 1H); 7.57 (d, J=7.6 Hz, NH—C$_6$H$_{11}$, 1H), 3.40 (m, CH—NH, 1H); 1.99 (t, J=7 Hz, CH$_2$CONHC$_6$H$_{11}$, 2H); 1.91 (t, J=7.6 Hz, CH$_2$CONHOH, 2H); 1.63 (m, 4H); 1.44 (m, 6H); 1.20 (m, 8H).

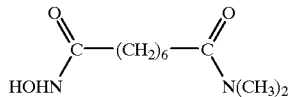

Yield 870 mg (20%). $^1$H NMR (DMSO-D$_6$, 200 MHZ), δ(ppm) 10.31 (s, NHOH, 1H); 8.67 (s, broad, NHOH, 1H); 2.85 (d, J=30 Hz, N(CH$_3$)$_2$, 6H); 2.24 (t, J=7.4 Hz, CH$_2$CON(CH$_3$), 2H); 1.91 (t, J=7.4 Hz, CH$_2$COONHOH, 2H); 1.50 (m, 4H); 1.20 (m, 4H).

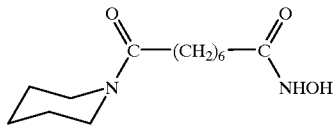

Yield 1.4 g (27%); $^1$H NMR (DMSO-d$_6$, 200 MHz), δ(ppm) 10.31 (s, NHOH, 1H); 8.67 (s, NHOH, 1H); 3.40 (2t, CH$_2$N, 4H); 2.20 (t, J=7.4 Hz, CH$_2$CON(CH$_2$)$_5$, 2H); 1.91 (t, J=7.4 Hz, CH$_2$CONHOH, 2H); 1.10–1.60 (m, broad, 14 H).

Compound having structure:

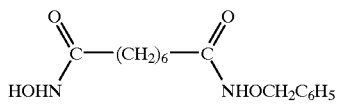

The chloroform (500 mL) solution of O-benzylhydroxylamine (1.23 g; 0.01 mol), O-(trimethylsilyl)hydroxylamine (1.1 g; 0.01 mol), pyridine (1.6 mL; 1.7 g; 0.02 mol) and suberoyl chloride (1.8 mL; 2.11 g; 0.01 mol) was stirred at room temperature overnight. The reaction suspension was diluted with methanol (100 mL), washed with 10% hydrochloric acid (3×100 mL). The organic layer was dried over anhydrous magnesium sulfate and evaporated. The solid residue was subjected to chromatography on silica gel in ethyl acetate-tetrahydrofuran (4:1). The yield was 500 mg (17%). $^1$H NMR (DMSO-d$_6$, 200 MHz), δ(ppm) 11.09 (s, NHOCH$_2$C$_6$H$_5$, 1H); 10.31 (s, NHOH, 1H); 8.67 (s, broad, NHOH, 1H); 7.36 (s, C$_6$H$_5$, 5H), 4.76 (s, CH$_2$C$_6$H$_5$, 2H); 1.92 (t, J=7.4 Hz, CH$_2$CO—, 4H); 1.45 (m, 4H); 1.20 (m, 4H).

Compound having the structure:

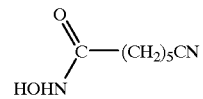

Into a cooled solution of potassium hydroxide (2.24 g; 0.04 mol) and O-benzylhydroxylamine hydrochloride in 30 mL of tetrahydrofuran-water (1:1) mixture, 6-bromohexanoyl chloride (3.1 mL; 4.27 g; 0.02 mol) was added. The reaction mixture was stirred at room temperature for one hour. The solvent was evaporated and solid residue was partitioned between chloroform (200 mL) and water (100 mL). Chloroform layer was washed with 10% hydrochloric acid (3×50 mL) and water (2×50 mL). The organic layer was dried over anhydrous magnesium sulfate and evaporated. The product was purified by crystallization from ethyl acetate-hexanes. The yield of N-benzyloxy-6-bromohexanoyl amide was 4.7 g (78%). A dimethylsulfoxide (250 mL) solution of N-benzyloxy-6-bromohexanoyl amide (4.5 g; 15 mmol) and sodium cyanide (7.35 g; 0.15 mol) was heated at 130° C. overnight. The solvent was evaporated and solid residue was partitioned between chloroform (300 mL) and water (300 mL). The chloroform layer was washed with water (5×100 mL), dried over anhydrous magnesium sulfate, and evaporated. The oily residue was purified by column chromatography on silica gel in ethyl acetate-tetrahydrofuran (4:1) as an eluent. The yield of N-benzyloxy-6-cyanohexanoylamide was 1.62 g (43%). The product was dissolved in methanol (50 mL) and 5% Pd-C (100 mg) was added. The black suspension was shaken under hydrogen pressure (~50 psi) overnight. The catalyst was isolated by filtration and filtrate was evaporated. The solid residue was slurried in hexanes (~20 mL) and filtered. The yield of N-hydroxy-6-cyanohexanoylamide was 900 mg (overall yield 30%). $^1$H NMR (DMSO-d$_6$, 200 MHz), δ(ppm) 10.32 (s, NHOH, 1H); 8.65 (s, NHOH, 1H); 2.45 (t, J=7 Hz, CH$_2$CN, 2H) 1.93 (t, J=7 Hz, CH$_2$CONHOH, 2H); 1.49 (m, 4H); 1.33 (m, 2H).

Compounds having the structure:

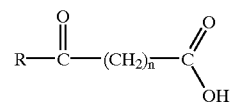

General Procedure

A diacid dichloride (0.01 mol) was added into a cooled (0° C.) solution of potassium hydroxide (1.12 g; 0.02 mol) and corresponding amine (0.01 mol) in 30 mL of tetrahydrofuran-water (1:1) mixture. The reaction mixture was stirred at room temperature about one hour. Solvent was evaporated and the solid residue was partitioned between chloroform (300 mL) and water (300 mL). In some cases a small amount of methanol is necessary to dissolve all solid. The organic layer was washed with 10% potassium hydroxide (3×30 mL). The basic water extract was acidified with 10% hydrochloric acid. The precipitate was collected by filtration, dried and purified by crystallization from ethyl acetate or by column chromatography on silica gel in ethyl acetate-tetrahydrofuran (4:1). The yields are from 20–37%.

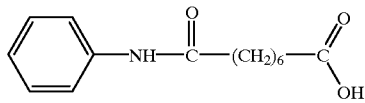

$^1$H NMR (DMSO-$d_6$, 200 MHz), δ(ppm) 11.97 (s, COOH, 1H); 9.84 (s, NH, 1H); 7.57 (d, J=7.4 Hz, ortho aromatic protons, 2H);

7.26 (t, J=8.4 Hz, meta aromatic protons, 2H); 6.99 (t, J=7.4 Hz, para aromatic proton, 1H), 2.27 (t, J=7 Hz, CH$_2$CONHPh, 2H); 2.18 (t, J=7.2 Hz, 2H); 1.52 (m, 4H); 1.28 (m, 4H).

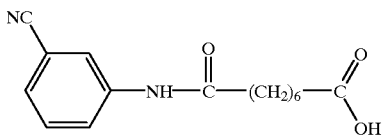

$^1$H NMR (DMSO-$d_6$, 200 MHz), δ(ppm) 11.95 (s, COOH, 1H); 10.20 (s, NH, 1H); 8.10 (s, aromatic proton, 1H); 7.75 (m, aromatic proton, 1H); 7.45 (m, aromatic proton, 2H); 2.28 (t, J=7.4 Hz, CH$_2$CONHAr, 2H); 2.21 (t, J=7.2 Hz, CH$_2$COOH, 2H); 1.46 (m, 4H); 1.20 (m, 4H).

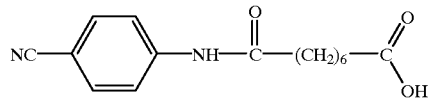

$^1$H NMR (DMSO-$d_6$, 200 MHz), δ(ppm) 11.95 (s, COOH, 1H); 10.29 (s, NH, 1H); 7.75 (s, aromatic protons, 4H); 2.33 (t, J=7.2 Hz, CH$_2$CONHAr, 2H); 2.18 (t, J=7.4 Hz, CH$_2$COOH, 2H); 1.53 (m, 4H); 1.27 (m, 4H).

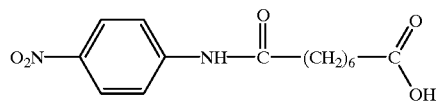

$^1$H NMR (DMSO-$d_6$, 200MHz), 11.98 (s, broad, COOH, 1H); 10.48 (s, NH, 1H); 8.21 (d, J=9.2 Hz, aromatic protons, 2H); 7.82 (d, J=9.2 Hz, aromatic proton, 2H); 2.36 (t, J=7.4 Hz, CH$_2$CONHAr, 2H); 2.18 (t, J=7.2 Hz, CH$_2$COOH, 2H); 1.55 (m, 4H); 1.29 (m, 4H).

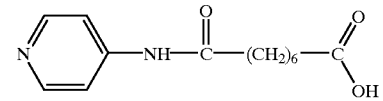

$^1$H NMR (DMSO-$d_6$, 200 MHz), δ(ppm) 12.00 (s, broad COOH, 1H); 10.24 (s, NH, 1H); 8.38 (d, J=5.8 Hz, aromatic protons, 2H); 7.55 (d, J=5.8 Hz, aromatic protons, 2H); 2.33 (t, J=7.2 Hz, CH$_2$CONHAr, 2H); 2.18 (t, J=7.2 Hz, CH$_2$COOH); 1.52 (m, 4H); 1.27 (m, 4H).

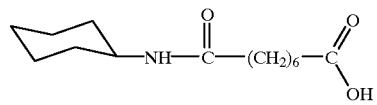

$^1$H NMR (DMSO-$d_6$, 200MHz), δ (ppm) 11.95 (s, COOH, 1H); 7.58 (d, J=8 Hz); 3.50 (m, CH, 1H); 2.17 (t, J=7.2HZ, CH$_2$COOH, 2H); 2.00 (t, J=7 Hz, CH$_2$CONH—, 2H); 1.60 (m, 4H); 1.46 (m, 6H); 1.20 (m, 8H).

In the same way the following compounds were prepared and characterized:

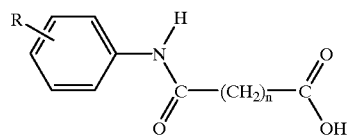

wherein n=4, 5, 6, 7, and 8; R is hydrogen; 2-, 3-, and 4-cyano; 2-, 3-, and 4-nitro; 2-, 3-, and 4-methylcyano; 2-, 3-, and 4-trifluoromethyl; 2-, 3-, and 4-fluoro;

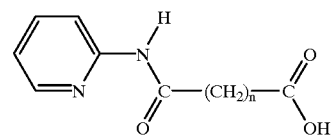

wherein n=4, 5, 6, 7, and 8;

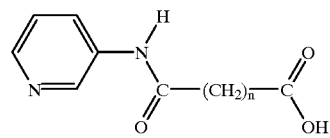

wherein n=4, 5, 6, 7, and 8;

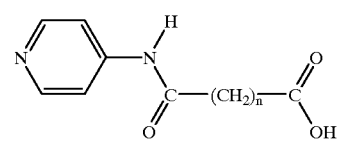

wherein n=4, 5, 6, 7, and 8;

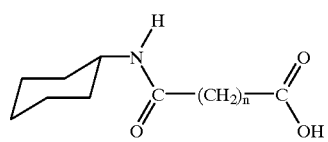

wherein n=4, 5, 6, 7, and 8;

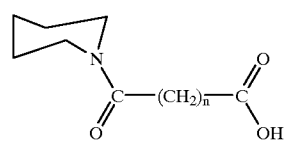

wherein n=4, 5, 6, 7, and 8;

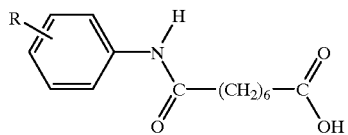

wherein R is 2-, 3-, and 4-carboxy; 2-, 3-, and 4-aminocarbonyl; 2-, 3-, and 4-methylaminocarbonyl; 2-, 3-, and 4-dimethylaminocarbonyl; 2-, 3-, and 4-chloro; 2-, 3-, and 4-bromo; 2-, 3-, and 4-iodo; 2-, 3, and 4-methyl; 2-, 3-, and 4 methoxy; 2-, 3-, and 4-hydroxy.; 2-, 3-, and 4-amino; and 2-, 3-, and 4-dimethylamino.

Compounds having the general structure:

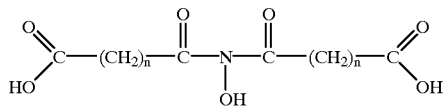

wherein n=4, 5, 6, and 7.

General Procedure A

A pyridine (500 mL) suspension of O-benzylhydroxylamine hydrochloride (3.2 g; 0.02 mol) and the corresponding diacid dichloride (0.04 mol) was stirred at room temperature for three days. Water (10 mL) was added and stirring was continued overnight. The solvent was evaporated and solid residue was purified by column chromatography on silica gel in tetrahydrofuran-methanol. The diacid product was dissolved in methanol (100 mL) and 5% Pd-C (100 mg) was added. The reaction suspension was shaken overnight under hydrogen pressure (~50 psi). The catalyst was separated by filtration, solid residue was washed with hot methanol (5×50 ml). The combined methanolic filtrates were evaporated. The solid residue was slurried in acetone and filtered. The yield was 10–20%.

General Procedure B

A pyridine (500 ml) solution of O-benzylhydroxylamine (2.46 g; 0.02 mol) and the corresponding dicarboxylic acid monobenzyl ester monoacid chloride (0.04 mol) was stirred at room temperature overnight. The solvent was evaporated.

The semisolid residue was dissolved in chloroform (300 mL) and extracted with 5% hydrochloric acid (2×50 mL), 10% potassium hydroxide (3×100 mL), and water (2×100 mL). The organic layer was dried over anhydrous magnesium sulfate and evaporated. The solid residue was purified by column chromatography on silica gel in ethyl acetate. The tribenzyl product was dissolved in methanol (100 mL) and 5% Pd-C (100 mg) was added. The reaction suspension was shaken under hydrogen pressure (~50 psi) at room temperature overnight. The solid was separated by filtration and washed with hot methanol (5×50 mL). The combined methanol filtrates were evaporated to solid residue. The solid residue was slurried in cooled acetone and filtered. The yield of target product was 30–60%.

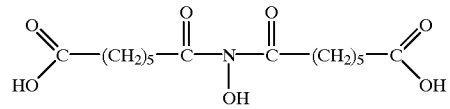

$^1$H NMR (DMSO-$d_6$, 200MHz), δ(ppm) 11.53 (s, COOH, 1H); 2.41 (t, J=7.2 Hz, CH$_2$CON(OH)COCH$_2$, 4H); 2.18 (t, J=7.0 Hz, CH$_2$COOH, 4H); 1.52 (m, 8 h); 1.22 (m, H). MS (FAB, glycerin) 346(M+1)

Compounds having the Structure:

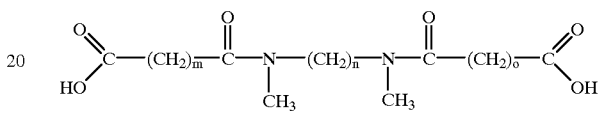

A pyridine (500 mL) solution of the monomethyl ester monoacid chloride of dicarboxylic acid (0.02 mol) and N,N'-dimethyl-1, x-diaminoalkane (0.01 mol) was stirred at room temperature overnight. Solvent was evaporated and oily residue was dissolved in chloroform (300 mL). Chloroform solution was washed with water (3×50 mL), 10% potassium hydroxide (3×50 mL), 10% hydrochloric acid (3×50 mL), and again with water (3×50 mL). The organic layer was dried and evaporated. The oily residue was dissolved in potassium hydroxide (1.2 g; 0.021 mol) in 80% methanol (100 mL). The reaction mixture was refluxed two hours. The solvent was evaporated and solid residue was dissolved in water (50 mL) and extracted with chloroform (3×50 mL).

Water solution was acidified to pH~5 and concentrated (to volume of about 10 mL). The water solution or suspension was cooled down and precipitate was separated by filtration. The solid product was purified by crystallization from ethyl acetate. The yield was 40–60%.

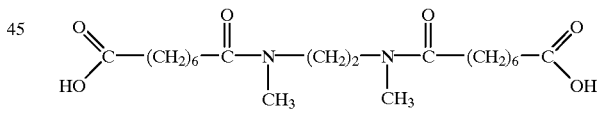

$^1$H NMR (CDCl$_3$, 200 MHz), δ(ppm) 8.15 (s, broad, COOH, 2H); 3.52+3.45 (2s, CH$_2$N, 4H); 3.01+2.93 (2s, CH$_3$N, 6H); 2.30 (4t, CH$_2$CO, 8H); 1.60 (m, 8H); 1.32 (m, 8H). $^1$H NMR (DMSO-$d_6$, 200 MHz), δ(ppm) 3.44+3.336+3.36 (3s, CH$_2$N, 4H); 2.94+2.90+2.79 (3s, CH$_3$N, 6H); 2.27+2.23+2.12 (3t, CH$_2$CO, 8H); 1.46 (m, 8H): 1.23 (m, 8H).

Compounds having the Structure:

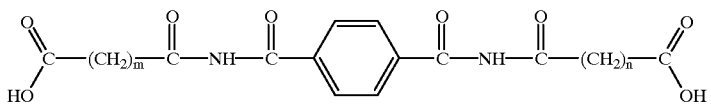

A pyridine (500 mL) solution of 6-aminocapric acid (2.6 g; 0.02 mol) and terephthaloyl chloride (2 g; 0.01 mol) was stirred at room temperature overnight (~12 hours), and at 90° C. for 23 hours. The solvent was evaporated, and the solid residue was crystallized from water (10 mL) four times. The yield was 800 mg (19%). $^1$H NMR (DMSO-$d_6$, 200 MH), δ(ppm) 12.8 (s, broad, COOH, 2H); 8.54+7.72 (2t, NH, 2H); 3.24+2.98 (2m, NHCH$_2$, 4H); 2.20+2.03 (2m, CH$_2$CO, 4H); 1.50 (m, 8H); 1.32 (m, 4H).

Compound Having the Structure:

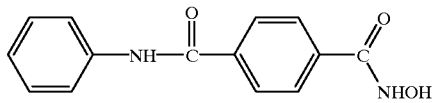

Into a mixture of aniline (2.75 g; 0.03 mol), hydroxylamine hydrochloride (2.08 g; 0.03 mol), and potassium hydroxide (5.50 g; 0.09 mol) in 50% tetrahydrofuran (100 mL) was slowly added at room temperature a tetrahydrofurane (20 mL) solution of terephthaloyl chloride (6 g; 0.03 mol). The reaction suspension was stirred at room temperature for thirty minutes. The solvent was evaporated. The solid residue was slurried in hot methanol (1000 mL) and dried over anhydrous magnesium sulfate. The methanol solution was separated by filtration and filtrate was evaporated. The solid residue was slurried in 20 mL cooled methanol and filtered. The white crystals were washed with ether (5×50 mL) and dried. The yield was 4.6 g (39%). $^1$H NMR (DMSO-$d_6$, 200 MHz), δ(ppm) 11.35 (s, broad, NHOH, 1H); 10.35 (s, NHPh, 1H); 9.19 (s, NHOH, 1H); 8.03 (d, J=8 Hz, terephthalic protons, 2H); 7.89 (d, J=8 Hz, terephthalic protons, 2H); 7,82 (d, J=7.4 Hz, ortho anilide protons, 2H); 7.34 (t, J=7.4 Hz, meta anilide protons, 2H); 7.10 (t, J=7.4 Hz, para anilide proton, 1H).

Compound Having the Structure:

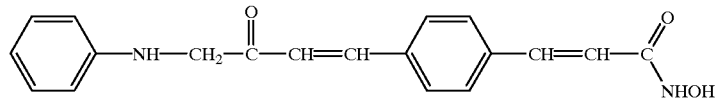

A solution of 1,4-phenylenediacrylic acid (2.18 g; 0.01 mol) in thionyl chloride (50 mL; 81.55 g; 0.68 mol) was refluxed overnight. The excess of thionyl chloride was evaporated. The solid was dissolved in tetrahydrofuran (20 mL), and added to a cooled (0° C.) solution of potassium hydroxide (1.12 g; 0.02 mol) and aniline in 50% tetrahydrofuran. The reaction mixture was stirred at room temperature for thirty minutes. The solvent was evaporated. The solid residue was slurried in water and filtered. White crystals were dissolved in a small amount of methanol and purified on a silica gel column in tetrahydrofuran. The yield was 315 mg (10%). $^1$H NMR (DMSO-$d_6$, 200 MHz), δ(ppm) 10.80 (s, NHOH, 1H); 10.23 (s, NHPh, 1H); 9.09 (s, NHOH, 1H); 7.69 (d, J=7.6 Hz, ortho anilide protons, 2H); 7.64 (s, phenylene protons, 4H), 7.55 (d, J=15.8 Hz, PhNHOCCH═CH—, 1H); 7.40 (d, J=15.8 Hz, HONHOCCH=CH—, 1H); 7.33 (t, J=7.8 Hz, meta anilide protons, 2H); 7.06 (t, J=7.2 Hz, para anilide protons, 1H); 6.89 (d, J=15.8 Hz, PhNHOCCH═CH—, 1H) 6.51 (d, J=15.8 Hz, HOHNOCCH═CH—, 1H).

Compounds having the Structure:

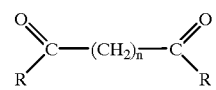

wherein n=4, 5, 6, 7, and 8.

A chloroform solution of triethylamine (1.4 mL; 1.0 g; 0.01 mol), the corresponding amine (0.01 mol) and diacid dichloride (0.005 mol) was stirred at room temperature for five hours. If the reaction mixture was clear, it was washed with water (5×100 mL). The organic layer was dried over anhydrous magnesium sulfate and evaporated to a solid residue. If in the course of reaction a precipitate was formed, the precipitate was separated by filtration. White crystals from filtration or solid residue from evaporation were crystallized from ethyl acetate, tetrahydrofuran, methanol, or their mixture. The yields were from 60–90%.

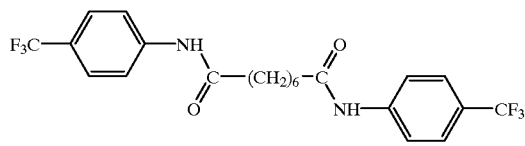

$^1$H NMR (DMSO-$d_6$, 200 MHz), δ(ppm) 10.23 (s, NH, 2H); 7.82 (d, J=9 Hz, aromatic protons, 4H), 7.60 (d, J=9 Hz, aromatic protons, 4H), 2.31 (t, J=7.4 Hz, CH$_2$CO, 4H); 2.61 (m, 4H); 1.32 (m, 4H).

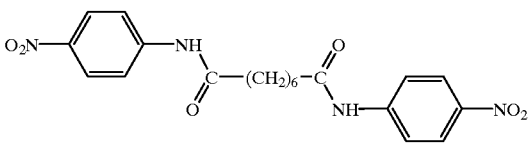

$^1$H NMR (DMSO-$d_6$, 200 MHz), δ(ppm) 10.48 (s, NH, 2H); 8.18 (d, J=9.2 Hz, aromatic protons, 4H); 7.81 (d, J=9.2 Hz, aromatic protons, 4HO; 2.37 (t, J=7.2 Hz, CH$_2$CO—, 4H); 1.60 (m, 4H); 1.33 (m, 4H).

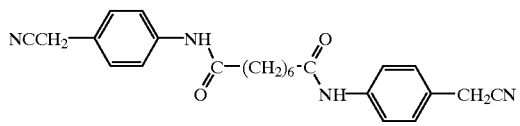

¹H NMR (DMSO-d₆, 200 MHz), 69.91 (s, NH, 2H), 7.58 (d, J=8.6 Hz, aromatic protons, 4H); 7.26 (d, J=8.6 Hz, aromatic protons, 4H); 3.94 (s, CH₂CN, 4H); 2.29 (t, J=7.4 Hz, CH₂CO—, 4H); 1.60 (m, 4H); 1.31 (m, 4H).

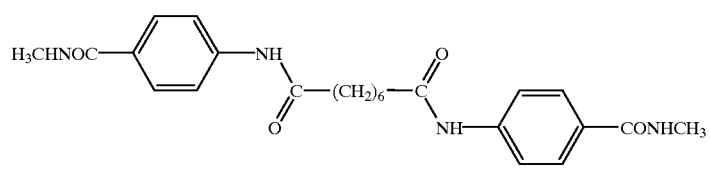

¹H NMR (DMSO-d₆, 200 MHz), δ(ppm) 10.08 (s, CONHAr, 2H); 7.79 (d, J=8.6 Hz, aromatic protons, 4H); 7.63 (d, J=8 Hz, aromatic protons, 4H), 7.22 (s, H₃CHNCO—, 2H); 3.32 (s, CH₃, ₆H); 2.31 (t, J=7 Hz, CH₂C—), 6H); 1.59 (m, 4H); 1.31 (m, 4H).

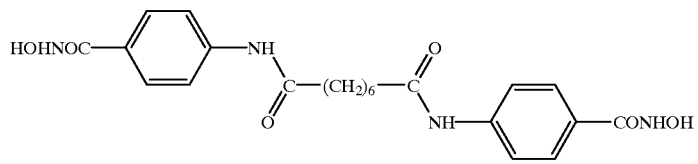

¹H NMR (DMSO-d₆, 200 MHz), δ(ppm) 10.90 (s, broad, NHOH, 2H); 10.05 (s, NHAr, 2H); 8.90 (s, broad, NHOH, 2H); 7.68 (d, J=9 Hz, aromatic protons, 4H); 7.62 (d, J=9 Hz, aromatic protons, 4H); 2.31 (t, J=7.2 Hz, CH₂CO—, 4H); 1.59 (m, 4H); 1.30 (m, 4H).

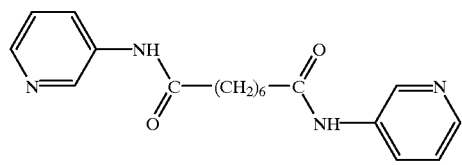

¹H NMR (DMSO-d6, 200 MHz), δ(ppm) 10.06 (s, broad, NH, 2H); 8.71 (d, J=2.6 Hz, aromatic protons, 2H); 7.31 (d+d, aromatic protons, 2H); 2.32 (t, J=7.4 Hz, CH₂CO—, 4H); 1.59 (m, 4H); 1.33 (m, 4H).

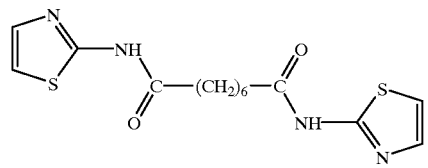

¹H NMR (DMSO-d₆, 200 MHz), δ(ppm) 12.00 (s, broad, NH, 2H);

7.43 (d, J=3.6 Hz, aromatic protons, 2H); 7.16 (d, J=3.6 Hz, aromatic protons, 2H); 2.41 (t, J=7.2 Hz, CH₂CONH—, 4H) 1.58 (m, 4H); 1.28 (m, 4H).

In the similar manner, the following compounds were prepared and characterized:

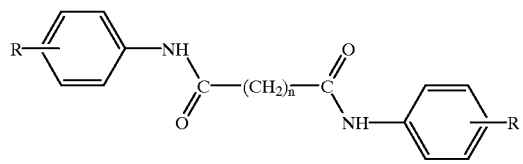

wherein n=4, 5, 6, 7, and 8; all compounds are symmetrical wherein R is 2-, 3-, and 4-cyano; 2-, 3-, and 4-methylcyano; 2-, 3-, and 4-nitro, 2-, 3-, and 4-carboxy; 2-, 3-, and 4-aminocarbonyl; 2-, 3- and 4-methylaminocarbonyl; 2-, 3-, and 4-dimethylaminocarbonyl; and 2-, 3-, and 4-trifluoromethyl;

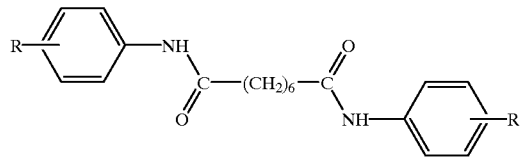

wherein R is 4-hydroxylaminocarbonyl; 4-methoxycarbonyl; 2-, 3-, and 4-chloro; 2-, 3-, and 4-fluoro; 2-, 3-, and 4-methyl; 2-, 3-, and 4-methoxy; 2,3-difluoro; 2,4-difluoro; 2,5-difluoro; 2,6-difluoro; 1,2,3,-trifluoro, 3,4,5-trifluoro; 2,3,5,6-tetrafluoro; 2,3,4,5,6-pentafluoro.

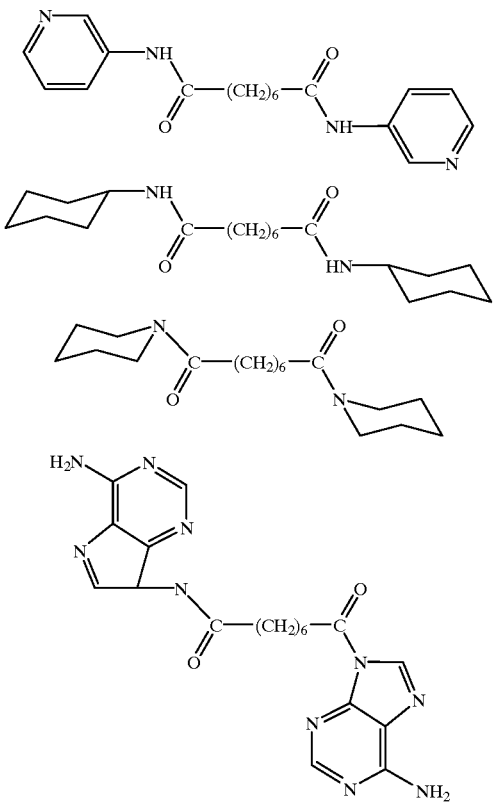

Compounds having the Structure:

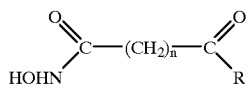

wherein n=4, 5, 6, 7, and 8.

General Procedure A

A diacid dichloride (0.01 mol) was added to a stirred solution of potassium hydroxide (1.68 g; 0.03 mol), hydroxylamine hydrochloride (0.7 g; 0.01 mol), and the corresponding aniline (0.01 mol) in 50% tetrahydrofuran (100 mL). The resulting reaction mixture was stirred at room temperature thirty minutes, and solvent was evaporated to solid residue. The solid residue was slurried in methanol (~100 mL) and dried over anhydrous magnesium sulfate. The methanol solution was separated by filtration and evaporated to a solid residue. The product was purified by column chromatography on silica gel in ethyl acetate tetrahydrofuran (in most cases 3:1). The yields were 15–30%.

General Procedure B

A solution of corresponding monomethyl ester of dicarboxylic acid (0.01 mol), oxaloyl chloride (0.03 mol), and a few drops DMF in benzene (500 mL) was stirred at room temperature overnight. The solvent was evaporated and the oily residue was dissolved in dry benzene (3×50 mL) and evaporated again. The tetrahydrofuran (50 mL) solution of monoester monoacid chloride of the corresponding dicarboxylic acid was slowly added to a cooled solution of the corresponding amine (0.01 mol) and pyridine (1.6 mL; 1.6 g; 0.02 mol) in tetrahydrofuran (200 mL). The reaction mixture was stirred at room temperature for an hour. The solvent was evaporated, the reside was dissolved in chloroform (300 mL), and the chloroform solution was washed with 10% hydrochloric acid (3×50 mL), 10% potassium hydroxide (3×50 mL), and water (3×50 mL). The organic layer was dried over anhydrous magnesium sulfate and evaporated, yielding the pure monoester monoamide of dicarboxylic acid. The product was dissolved in 80% methanol with potassium hydroxide (0.56 g; 0.01 mol). The reaction mixture was refluxed two hours and evaporated to solid residue. The residue was dissolved in water (~20 mL) and acidified to ~pH 5 with 10% hydrochloric acid. The monoacid monoamide of the dicarboxylic acid was isolated by filtration of precipitate or extraction water solution with chloroform. The isolated monoacid monoamide of the dicarboxylic acid was mixed together with an equivalent amount of O-benzylhydroxylamine and 1,3-dicyclohexylcarbodiimide in pyridine (~100 mL per 0.01 mol of O-benzylhydroxylamine) and was stirred at room temperature overnight. The solvent was evaporated and the solid residue was partitioned between chloroform (500 mL) and 10% hydrochloric acid (300 mL). The organic layer was washed with water (3×100 mL) and dried over anhydrous magnesium sulfate. The solvent was evaporated to solid residue. The solid residue was dissolved in large amounts of tetrahydrofuran and filtered through a short column of silica gel. The crude product was dissolved in methanol (100 mL) and 5% Pd-C was added. The reaction suspension was shaken under hydrogen pressure (~50 psi) overnight. The catalyst was separated by filtration and filtrate was evaporated to solid residue. The solid residue was slurried in hexanes and filtered. Mostly pure product was isolated in this way. If necessary further purification was achieved by column chromatography on silica gel with ethyl acetate tetrahydrofuran. The yields were from 35% to 65%.

General Procedure C

A pyridine (500 mL solution of O-benxylhydroxylamine (1.23; 0.01 mol), the corresponding amine (0.01 mol), and the dichloride of the dicarboxylic acid (0.01 mol) was stirred at room temperature overnight. The solvent was evaporated and the white solid residue contains, judged by $^1$H NMR, two symmetrical amides and a target unsymmetrical one. The solid residue was slurried in methanol and dried over anhydrous magnesium sulfate. The filtrate was evaporated and the solid residue was dissolved in methanol (~100 mL). Into the methanol solution 5% Pd-C (100 mg) was added and the black suspension was shaken under hydrogen pressure (~50 psi) overnight. The catalyst was separated by filtration and the filtrate was evaporated. The product was isolated by column chromatography on silica with ethyl acetate tetrahydrofuran. The yields were from 20% to 35%.

General Procedure D

A chloroform solution of triethylamine (3 mL; 2.18 g; 0.0215 mol), the corresponding amine (0.01 mol), O-trimethylsilyl)hydroxylamine (1.05 g, 0.01 mol), and the corresponding diacid chloride of the dicarboxylic acid (0.01 mol) was stirred at room temperature overnight. The solvent was evaporated, the residue was dissolved in methanol (~10 mL), and into the methanol solution 10% ammonium chloride (~10 mL) was added. The resulting suspension was stirred at 50° C. for two hours. The solvent was evaporated. The solid residue was slurried in methanol (300 mL) and dried over anhydrous magnesium sulfate. The methanol solution was separated by filtration and evaporated to a solid residue. The product was isolated by silica gel column chromatography with ethyl acetate-tetrahydrofuran. The yields were 20–33%.

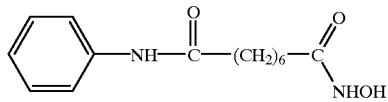

Elemental analysis: Calc. 63.62 7.63 10.60

Found 63.58 7.59 10.48

$^1$H NMR (DMSO-$d_6$, 200 MHz), δ(ppm) 10.31 (s, NHOH, 1H); 9.83 (s, NHPh, 1H); 8.64 (s, NHOH, 1H); 7.57 (d, J=8.2 Hz, ortho aromatic protons, 2H); 7.26 (t, J=8.4 Hz, meta aromatic protons, 2H), 6.99 (t, J=7.4 Hz, para aromatic protons, 1H); 2.27 (t, J=7.4 Hz, CH$_2$CONHPh, 2H); 1.93 (t, J=7.2 Hz, CH$_2$CONHOH, 2H); 1.52 (m, 4H); 1.26 (m, 4H). MS (Fab, Glycerin) 172, 204, 232, 249, 265, (100%, M+1).

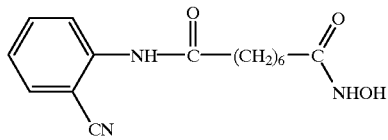

$^1$H NMR (DMSO-$d_6$, 200 MHz), δ(ppm) 10.31 (s, NHOH, 1H); 10.08 (s, NHPh, 1H); 8.64 (s, NHOH, 1H); 7.78 (d, J=7.6 Hz, aromatic protons, 1H); 7.66 (t, J=7.4 Hz, aromatic protons, 1H); 7.48 (d, J=7.8 Hz, aromatic protons, 1H); 7.29 (t, J=7.4 Hz, aromatic protons, 1H); 2.34 (t, J=7 Hz, CH$_2$CONHAr, 2H); 1.93 (t, J=7.4 Hz, CH$_2$CONHOH, 2H); 1.58 (m, 4H); 1.27 (m, 4H).

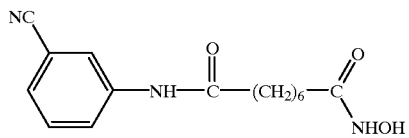

$^1$H NMR (DMSO-$d_6$, 200 MHz), δ(ppm) 10.31 (s, NHOH, 1H); 10.21 (s, NHPh, 1H); 8.65 (s, NHOH, 1H); 8.09 (s, aromatic proton, 1H); 7.77 (m, aromatic proton, 1H); 7.49 (m, aromatic proton, 1H); 2.31 (t, J=7.2 Hz, CH$_2$CONHAr, 2H); 1.93 (t, J=7.2 Hz, CH$_2$CONHOH, 2H); 1.51 (m, 4H).

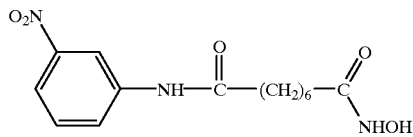

$^1$H NMR (DMSO-$d_6$, 200 MHz), δ(ppm) 10.35 (s, NHAr, 1H); 10.31 (s, NHOH, 1H); 8.63 (s, NHOH+aromatic proton 2H); 7.88 (d, J=8 Hz, aromatic protons, 2H); 7.57 (t, J=8 Hz, aromatic proton, 1H); 2.33 (t, J=7.6 Hz, CH$_2$CONHAr, 2H); 1.93 (t, J=7.4 Hz, CH$_2$CONHOH, 2H), 1.52 (m, 4H); 1.27 (m, 4H).

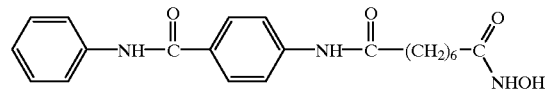

$^1$H NMR (DMSO-$d_6$, 200 MHz), δ(ppm) 10.33 (s, NHOH, 1H); 10.15 (s, NHAr, 1H); 10.09 (s, NHPh, 1H); 8.66 (s, NHOH, 1H); 7.91 (d, J=8.6 Hz, aromatic protons, 2H); 7.76 (d, J=7.8 Hz, ortho aniline protons, 2H); 7.71 (d, J=8.6 Hz, aromatic protons, 2H); 7.33 (t, J=7.6 Hz, meta anilide protons, 2H); 7.07 (t, J=7.4 Hz, para anilide protons); 2.33 (t, J=7.5 Hz, C 2H); 1.93 (t, J=7.2 Hz, CH$_2$CNHH, 2H); 1.51 (m, 4H); 1.28 (m, 4H).

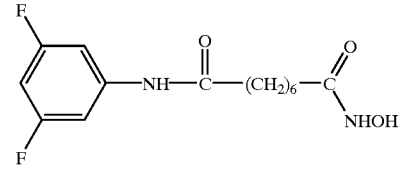

$^1$H NMR (DMSO-$d_6$, 200 MHz), δ(ppm) 10.32 (s, NHOH, 1H); 10.21 (s, NHAr, 1H); 8.65 (s, NHOH, 1H); 7.31 (d of d, J=10 Hz(2.2 Hz), aromatic protons, 2H); 6.84 (t of t, J=9.4 Hz(2.4 Hz), aromatic protons, 1H); 2.29 (t, CH$_2$CONHAr, 2H); 1.93 (t, J=7.2 Hz, CH$_2$CONHOH, 2H); 1.51 (m, 4H); 1.26 (m, 4H).

In the same manner the following compounds were prepared and characterized:

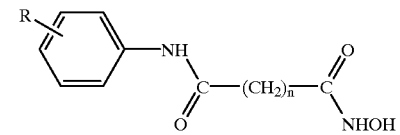

wherein n=4, 5, 6, 7, and 8; and R is 2-, 3-, and 4-cyano; 2-, 3-, and 4-methylcyano; 2-, 3-, and 4-nitro; 2-, 3-, and 4-carboxy; 2-, 3-, and 4-aminocarbonyl; 2-, 3-, and 4-methylaminocarbonyl; 2-, 3-, and 4-dimethylaminocarbonyl; and 2-, 3-, and 4-trifluoromethyl;

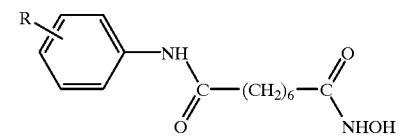

wherein R is 4-hydroxylaminocarbonyl; 4-methoxycarbonyl; 4-tetrazoyl; 2-, 3-, and 4-chloro; 2-, 3-, and 4-fluoro; 2-, 3-, and 4-methyl; 2-, 3-, and 4-methoxy; 2,3-difluoro; 2,4-difluoro; 2,5-difluoro; 2,6-difluoro; 1,2,3-trifluoro; 3,4,5-trifluoro; 2,4,5-trifluoro; 2,4,6-trifluoro; 2,3,6-trifluoro; 2,3,5,6-tetrafluoro; 2,3,4,5,6-pentafluoro; 2-, 3-, and 4-phenyl; 2-, 3-, and 4-benzyloxy; 4-hexyl; and 4-t-butyl;

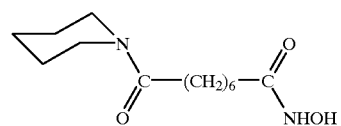

-continued

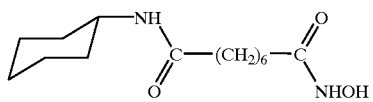

Compounds having the Structure:

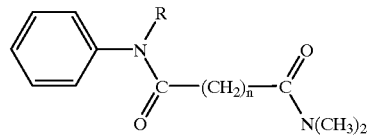

wherein n=4, 5, 6, 7, and 8; and R is hydrogen or methyl.

A diacid dichloride (0.01 mol) was added into a stirred solution of potassium hydroxide (1.68 g; 0.03 mol), aniline or N-methylaniline (0.01 mol), and dimethylamine hydrochloride (0.805 g; 0.01 mol) in 50% tetrahydrofuran (100 mL). The reaction mixture was stirred thirty minutes at room temperature. The solvent was partitioned between chloroform (400 mL) and water (300 mL). The organic layer was washed with 10% hydrochloric acid (3×100 mL), 10% potassium hydroxide (3×100 mL), and water (2×100 mL).

The organic layer was dried over anhydrous magnesium sulfate and evaporated. The solid residue was slurried in hexanes and filtered. The yield were 25–34%.

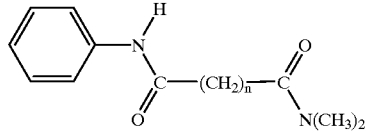

$^1$H NMR (DMSO-$d_6$, 200 MHz), δ(ppm) 9.82 (s, NHPh, 1H); 7.58 (d, J=7.6 Hz, ortho aromatic protons, 2H); 7.26 (t, J=7.4 Hz, meta aromatic protons, 2H); 6.99 (t, J=7.4 Hz, para aromatic proton, 1H); 2.85 (d, J=28 Hz, N(CH$_3$)$_2$, 6H); 2.28 (t, J=7.2 Hz, CH$_2$CO, 2H); 2.24 (t, J=7.4 Hz, CH$_2$CO, 2H); 1.51 (m, 4H); 1.29 (m, 4H).

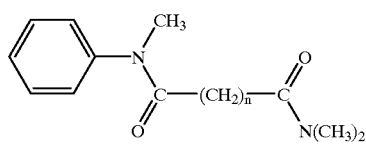

$^1$H NMR (DMSO-$d_6$, 200 MHz), δ(ppm) 7.30 (m, C6H$_5$, 5H); 3.13 (s, H3CNPh, 3H); 2.83 (d, J=26 Hz, N(CH$_3$)$_2$, 6H); 2.17 (t, J=7.6 Hz, CH$_2$CON(CH$_3$)$_2$, 2H); 1.98 (t, J=7.4 Hz, CH$_2$CON(CH$_3$)Ph, 2H); 1.41 (m, 4H); 1.11 (m, 4H).

TABLE 1

| CPD | Structure | Mol. Weight | Optimal Conc. (μM) | Benzidine Reactive Cells (%) |
|---|---|---|---|---|
| | ![structure with n] | | | |
| 1 | n = 4 (known compound) | 236 | 80 | 70 |
| 2 | n = 5 | 250 | 20 | 84 |
| 3 | n = 6 | 264 | 2.5 | 70 |
| 4 | n = 7 | 278 | 20 | 8 |
| 5 | n = 8 | 292 | 20 | 15 |
| 6 | [3-CN-phenyl structure with (CH$_2$)$_6$-OH] | 274 | 31 | 44 |
| 7 | [4-NC-phenyl structure with (CH$_2$)$_6$-OH] | 274 | 31 | 52 |
| 8 | [4-O$_2$N-phenyl structure with (CH$_2$)$_6$-OH] | 294 | 12.5 | 32 |

TABLE 1-continued

| CPD | Structure | Mol. Weight | Optimal Conc. (μM) | Benzidine Reactive Cells (%) |
|---|---|---|---|---|
| 9 | cyclohexyl-NH-C(O)-(CH₂)₆-C(O)-OH | 225 | 50 | 20 |
| 10 | PhCH₂O-C₆H₄-NH-C(O)-(CH₂)₆-C(O)-OH | 355 | 250 | 26 |
| 11 | (H₃C)₂N-C(O)-(CH₂)₆-C(O)-NHOH | 216 | 60 | 53 |
| 12 | HO-C(O)-(CH₂)₆-C(O)-NHOH | 189 | 250 | 35 |
| 13 | H₃CO-C(O)-(CH₂)₆-C(O)-NHOH | 203 | 60 | 17 |
| 14 | NC(CH₂)₅-C(O)-NHOH | 156 | 125 | 30 |
| 15 | H₃COHN-C(O)-(CH₂)₆-C(O)-NHOH | 218 | 20 | 43 |
| 16 | cyclohexyl-NH-C(O)-(CH₂)₆-C(O)-NHOH | 270 | 8 | 35 |
| 17 | piperidinyl-C(O)-(CH₂)₆-C(O)-NHOH | 256 | 62 | 30 |
| 18 | (CH₃)₃CONH-C(O)-(CH₂)₆-C(O)-NHOH | 260 | 31 | 38 |
| 19 | PhCH₂NH-C(O)-(CH₂)₆-C(O)-NHOH | 278 | 5 | 24 |
| | R-C₆H₄-NH-C(O)-(CH₂)₆-C(O)-NHOH | | | |

TABLE 1-continued

| CPD | Structure | Mol. Weight | Optimal Conc. (μM) | Benzidine Reactive Cells (%) |
|---|---|---|---|---|
| 20 | R = 4-methyl | 273 | 20 | 52 |
| 21 | R = 4-cyano | 289 | 7 | 70 |
| 22 | R = 3-cyano | 289 | 5 | 55 |
| 23 | R = 2-cyano | 289 | 16 | 65 |
| 24 | R = 3-nitro | 309 | 5 | 30 |
| 25 | R = 4-nitro | 309 | 0.8 | 30 |
| 26 | R = 3-trifluoromethyl | 332 | 30 | 30 |
| 27 | R = 4-trifluoromethyl | 332 | 5 | 47 |
| 28 | R = 2-amino | 279 | 20 | 54 |
| 29 | R = 4-cyanomethyl | 303 | 1 | 30 |
| 30 | R = 3-chloro | 298.5 | 2 | 33 |
| 31 | R = 4-azido (N$_3$) | 304 | 2 | 47 |
| 32 | R = 2-fluoro | 282 | 4 | 65 |
| 33 | R = 3-fluoro | 282 | 1 | 25 |
| 34 | R = 4-fluoro | 282 | 4 | 43 |
| 35 | R = 4-benzyloxy | 370 | 4 | 20 |
| 36 | R = 4-methyoxycarbonyl | 322 | 4 | 28 |
| 37 | R = 4-methylaminocarbonyl | 321 | 30 | 16 |
| 38 | R = 2-bromo | 343 | 8 | 45 |
| 39 | R = 2-chloro | 298.5 | 4 | 34 |
| 40 | R = 4-bromo | 343 | 1.6 | 47 |
| 41 | R = 2,3-difluoro | 300 | 8 | 24 |
| 42 | R = 2,4,5-trifluoro | 318 | 8 | 36 |
| 43 | R = 2,3,6-trifluoro | 318 | 31 | 53 |
| 44 | R = 2,4,6-trifluoro | 318 | 16 | 47 |
| 45 | R = 2,4-difluoro | 300 | 6 | 60 |
| 46 | R = 2,3,4,5,6-pentafluoro | 354 | 31 | 53 |
| 47 | R = 3,4-difluoro | 300 | 4 | 61 |
| 48 | R = 3,4,5-trifluoro | 318 | 8 | 55 |
| 49 | R = 2,5-difluoro | 300 | 4 | 70 |
| 50 | R = 3,5-difluoro | 300 | 2 | 73 |
| 51 | R = 2-methoxy | 294 | 8 | 36 |
| 52 | R = 3-methoxy | 294 | 6 | 38 |
| 53 | R = 4-methoxy | 294 | 6 | 37 |
| 54 | 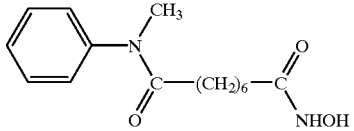 | 290 | 20 | 40 |
| 55 | 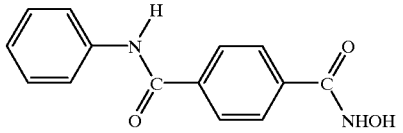 | 256 | 30 | 53 |
|  | 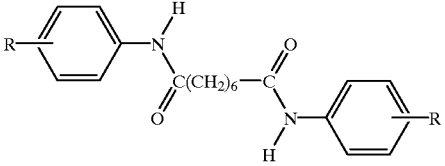 |  |  |  |
| 56 | R = 4-trifluoromethyl | 460 | 50 | 20 |
| 57 | R = 4(N)-hydroxylamino-carbonyl | 442 | 8 | 10 |
| 58 | R = 4-cyanomethyl | 402 | 50 | 25 |
| 59 | R = 2,4-difluoro | 396 | 500 | 54 |
| 60 | R = 2,6-difluoro | 396 | 100 | 21 |
| 61 | R = 3,5-difluoro | 396 | 125 | 31 |
| 62 | R = 2,3,6-trifluoro | 432 | 250 | 28 |
| 63 | R = 2,4,6-trifluoro | 432 | 125 | 35 |
| 64 | R = 2,3,4,5,6-pentafluoro | 504 | 125 | 13 |
| 65 | R = 4-nitro | 414 | 25 | 14 |

TABLE 1-continued

| CPD | Structure | Mol. Weight | Optimal Conc. (μM) | Benzidine Reactive Cells (%) |
|---|---|---|---|---|
| 66 | (H₃C)₂N-CO-CH(CH₃)-(CH₂)₅-CH(CH₃)-CO-N(CH₃)₂ | 270 | 1250 | 80 |
| 67 | (H₃C)₂N-CO-CH(CH₃)-(CH₂)₄-CH(CH₃)-CO-N(CH₃)₂ | 256 | 2500 | 90 |
| 68 | HOHN-CO-(CH₂)₂-CH(CH₃)-(CH₂)₂-CO-NHOH | 204 | 125 | 56 |
| 69 | HOHN-CO-(CH₂)₅-CH(CONHOH)-(CH₂)₅-CO-NHOH | 333 | 60 | 40 |
| 70 | HOHN-CO-(CH₂)₂-CF₂-(CH₂)₂-CO-NHOH | 226 | 160 | 19 |
|  | thiazol-2-yl-NH-CO-(CH₂)ₙ-CO-NH-thiazol-2-yl | | | |
| 71 | n = 4 | 310 | 100 | 8 |
| 72 | n = 5 | 324 | 250 | 10 |
| 73 | n = 6 | 338 | 50 | 7 |
| 74 | n = 7 | 352 | 100 | 10 |
| 75 | n = 8 | 366 | 100 | 10 |

TABLE 2

Induction of Differentiation of HL-60

| CPD | Mol. Weight | Optimal Conc. (μM) | NBT Positive (%) |
|---|---|---|---|
| 2 | 250 | 7 | 22 |
| 3 | 264 | 1 | 21 |
| 6 | 274 | 20 | 30 |
| 7 | 274 | 20 | 21 |
| 22 | 289 | 1.7 | 28 |
| 21 | 289 | 2 | 6 |
| 26 | 332 | 6 | 27 |
| 25 | 309 | 3 | 18 |
| 36 | 322 | 1 | 32 |
| 31 | 304 | 2.5 | 7 |
| 29 | 303 | 1 | 15 |
| 43 | 318 | 2 | 20 |

References

1. Sporn, M. B., Roberts, A. B., and Driscoll, J. S. (1985) in Cancer: Principles and Practice of Oncology, eds. Hellman, S., Rosenberg, S. A., and DeVita, V. T., Jr., Ed. 2, (J. B. Lippincott, Philadelphia), P. 49.
2. Breitman, T. R., Selonick, S. E., and Collins, S. J. (1980) Proc. Natl. Acad. Sci. USA 77: 2936–2940.
3. olsson, I. L. and Breitman, T. R. (1982) Cancer Res. 42: 3924–3927.
4. Schwartz, E. L. and Sartorelli, A. C. (1982) Cancer Res. 42: 2651–2655.
5. Marks, P. A., Sheffery, M., and Rifkind, R. A. (1987) Cancer Res. 47: 659.
6. Sachs, L. (1978) Nature (Lond.) 274: 535.
7. Friend, C., Scher, W., Holland, J. W., and Sato, T. (1971) Proc. Natl. Acad. Sci. (USA) 68: 378–382.
8. Tanaka, M., Levy, J., Terada, M., Breslow, R., Rifkind, R. A., and Marks, P. A. (1975) Proc. Natl. Acad. Sci. (USA) 72: 1003–1006.
9. Reuben, R. C., Wife, R. L., Breslow, R., Rifkind, R. A., and Marks, P. A. (1976) Proc. Natl. Acad. Sci. (USA) 73: 862–866.
10. Abe, E., Miyaura, C., Sakagami, H., Takeda, M., Konno, K., Yamazaki, T., Yoshika, S., and Suda, T. (1981) Proc. Natl. Acad. Sci. (USA) 78: 4990–4994.
11. Schwartz, E. L., Snoddy, J. R., Kreutter, D., Rasmussen, H., and Sartorelli, A. C. (1983) Proc. Am. Assoc. Cancer Res. 24: 18.
12. Tanenaga, K., Hozumi, M., and Sakagami, Y. (1980) Cancer Res. 40: 914–919.

13. Lotem, J. and Sachs, L. (1975) *Int. J. Cancer* 15: 731–740.
14. Metcalf, D. (1985) *Science*, 229: 16–22.
15. Scher, W., Scher, B. M., and Waxman, S. (1983) *Exp. Hematol.* 11: 490–498.
16. Scher, W., Scher, B. M., and Waxman, S. (1982) *Biochem. & Biophys. Res. Comm.* 109: 348–354.
17. Huberman, E. and Callaham, M. F. (1979) *Proc. Natl. Acad. Sci.* (USA) 76: 1293–1297.
18. Lottem, J. and Sachs, L. (1979) *Proc. Natl. Acad. Sci.* (USA) 76: 5158–5162.
19. Terada, M., Epner, E., Nudel, U., Salmon, J., Fibach, E., Rifkind, R. A., and Marks, P. A. (1978) *Proc. Natl. Acad. Sci.* (USA) 75: 2795–2799.
20. Morin, M. J. and Sartorelli, A. C. (1984) *Cancer Res.* 44: 2807–2812.
21. Schwartz, E. L., Brown, B. J., Nierenberg, M., Marsh, J. C., and Sartorelli, A. C. (1983) *Cancer Res.* 43: 2725–2730.
22. Sugano, H., Furusawa, M., Kawaguchi, T., and Ikawa, Y. (1973) *Bibl. Hematol.* 39: 943–954.
23. Ebert, P. S., Wars, I., and Buell, D. N. (1976) *Cancer Res*, 36: 1809–1813.
24. Hayashi, M., Okabe, J., and Hozumi, M. (1979) *Gann* 70: 235–238.
25. Fibach, E., Reuben, R. C., Rifkind, R. A., and Marks, P. A. (1977) *Cancer Res.* 37: 440–444.
26. Melloni, E., Pontremoli, S., Damiani, G., Viotti, P., Weich, N., Rifkind, R. A., and Marks, P. A. (1988) *Proc. Natl. Acad. Sci.* (USA) 85: 3835–3839.
27. Reuben, R., Khanna, P. L., Gazitt, Y., Breslow, R., Rifkind, R. A., and Marks, P. A. (1978) *J. Biol. Chem.* 253: 4214–4218.
28. Marks, P. A. and Rifkind, R. A. (1988) International *Journal of Cell Cloning* 6: 230–240.
29. Melloni, E., Pontremoli, S., Michetti, M., Sacco, O., Cakiroglu, A. G., Jackson, J. F., Rifkind, R. A., and Marks, P. A. (1987) *Proc. Natl. Acad. Sciences* (USA) 84: 5282–5286.
30. Marks, P. A. and Rifkind, R. A. (1984) *Cancer* 54: 2766–2769.
31. Egorin, M. J., Sigman, L. M. VanEcho, D. A., Forrest, A., Whitacre, M. Y., and Aisner, J. (1987) *Cancer Res.* 47: 617–623.
32. Rowinsky, E. W., Ettinger, D. S., Grochow, L. B., Brundrett, R. B., Cates, A. E., and Donehower, R. C. (1986) *J. Clin. Oncol.* 4: 1835–1844.
33. Rowinsky, E. L. Ettinger, D. S., McGuire, W. P., Noe, D. A., Grochow, L. B., and Donehower, R. C. (1987) *Cancer Res*, 47: 5788–5795.
34. Callery, P. S., Egorin, M. J., Geelhaar, L. A., and Nayer, M. S. B. (1986) *Cancer Res.* 46: 4900–4903.
35. Young, C. W. Fanucchi, M. P., Walsh, T. B., Blatzer, L., Yaldaie, S., Stevens, Y. W., Gordon, C., Tong, W., Rifkind, R. A., and Marks, P. A. (1988) *Cancer Res.* 48: 7304–7309.
36. Andreeff, M., Young, C., Clarkson, B., Fetten, J., Rifkind, R. A., and Marks, P. A. (1988) *Blood* 72: 186a.
37. Marks, P. A., Breslow, R., Rifkind, R. A., Ngo, L., and Singh, R. (1989) *Proc. Natl. Acad. Sci.* (USA) 86: 6358–6362.
38. Breslow, R., Jursic, B., Yan, Z. F., Friedman, E., Leng, L., Ngo, L., Rifkind, R. A., and Marks, P. A. (1991) *Proc. Natl. Acad. Sci.* (USA) 88: 5542–5546.
39. Ohta, Y., Tanaka, M., Terada, M., Miller, O. J., Bank, A., Marks, P. A., and Rifkind, R. A. (1976) *Proc. Natl. Acad. Sci.* (USA) 73: 1232–1236.
40. Collins, S. J., Gallo, R. C., and Gallagher, R. E. (1978) *Nature* (London) 270; 405–409.
41. Synder, S. W., Egorin, M. J., Geelhaar, L. A., Hamburger, A. W., and Callery, P. S. (1988) *Cancer Res.* 48; 3613–3616.

What is claimed is:

1. A method of selectively inducing terminal differentiation of neoplastic cells and thereby inhibiting proliferation of such cells which comprises contacting the cells under suitable conditions with an effective amount of the compound having the structure:

$$\underset{O}{\overset{R_1}{>}}C-(CH_2)_n-C\underset{R_2}{\overset{O}{<}}$$

wherein each of $R_1$ and $R_2$ are independently the same as or different from each other; when $R_1$ and $R_2$ are the same, each is a substituted or unsubstituted cycloalkylamino, pyridineamino, piperidino, 9-purine-6-amine, or thiazoleamino group; when $R_1$ and $R_2$ are different, $R_1=R_3-N-R_4$, wherein each of $R_3$ and $R_4$ are independently the same as or different from each other and are a hydrogen atom, a hydroxyl group, a substituted or unsubstituted, branched or unbranched alkyl, alkenyl, cycloalkyl, aryl, alkyloxy, aryloxy, arylalkyloxy, or pyridine group, or $R_3$ and $R_4$ bond together to form a piperidine group and $R_2$ is a hydroxylamino, hydroxyl, amino, alkylamino, or alkyloxy group; and n is an integer from 4 to 8, or a pharmaceutically acceptable salt thereof; and wherein the amount of the compound is effective to selectively induce terminal differentiation.

2. A method of claim 1 wherein the $R_1$ represents NHOH, $R_2$ represents OH, and n represents 6.

3. A method of claim 1 wherein the compound has the structure:

$$R_3-\underset{\overset{|}{C}}{N}\overset{R_4}{\underset{O}{-}}-(CH_2)_n-C\underset{R_2}{\overset{O}{<}}$$

wherein each of $R_3$ and $R_4$ are independently the same as or different from each other and are a hydrogen atom, a hydroxyl group, a substituted or unsubstituted, branched or unbranched alkyl, alkenyl, cycloalkyl, aryl, alkyloxy, aryloxy, arylalkyloxy, or pyridine group, or $R_3$ and $R_4$ bond together to form a piperidine group; $R_2$ is a hydroxylamino, hydroxyl, amino, alkylamino, or alkyloxy group; and n is an integer from 4 to 8, or a pharmaceutically acceptable salt thereof; and wherein the amount of compound is effective to selectively induce terminal differentiation.

4. A method of treating a patient having a tumor characterized by proliferation of neoplastic cells which comprises administering to the patient an effective amount of the compound having the structure:

$$\underset{O}{\overset{R_1}{>}}C-(CH_2)_n-C\underset{R_2}{\overset{O}{<}}$$

wherein each of $R_1$ and $R_2$ are independently the same as or different from each other; when $R_1$ and $R_2$ are the same, each is a substituted or unsubstituted cycloalkylamino, pyridineamino, piperidino, 9-purine-6-amine, or thiazoleamino group; when $R_1$ and $R_2$ are different, $R_1=R_3-N-R_4$, wherein each of $R_3$ and $R_4$ are independently the same as or different from each other and are a hydrogen atom, a hydroxyl group, a substituted or unsubstituted, branched or unbranched alkyl, alkenyl, cycloalkyl, aryl, alkyloxy, aryloxy, arylalkyloxy, or pyridine group, or $R_3$ and $R_4$ bond together to form a piperidine group and $R_2$ is a hydroxylamino, hydroxyl, amino, alkylamino, or alkyloxy group; and n is an integer from 4 to 8, or a pharmaceutically acceptable salt thereof; and wherein the amount of compound is effective to selectively induce terminal differentiation of such neoplastic cells and thereby inhibit their proliferation.

5. A method of claim 4 wherein the $R_1$ represents NHOH, $R_2$ represents OH, and n represents 6.

6. A method of claim 4 wherein the compound has the structure:

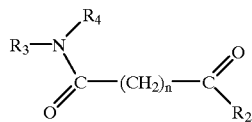

wherein each of $R_3$ and $R_4$ are independently the same as or different from each other and are a hydrogen atom, a hydroxyl group, a substituted or unsubstituted, branched or unbranched alkyl, alkenyl, cycloalkyl, aryl, alkyloxy, aryloxy, arylalkyloxy, or pyridine group, or $R_3$ and $R_4$ bond together to form a piperidine group; $R_2$ is a hydroxylamino, hydroxyl, amino, alkylamino, or alkyloxy group; and n is an integer from 4 to 8, or a pharmaceutically acceptable salt thereof; and wherein the amount of compound is effective to selectively induce terminal differentiation of such neoplastic cells and thereby inhibit their proliferation.

7. A method of claim 4 wherein the $R_2$ of the structure is a hydroxylamino, hydroxyl, amino, methylamino, or methyoxy group and n is 6.

8. A method of claim 4 wherein $R_4$ of the structure is a hydrogen atom and $R_3$ is a substituted or unsubstituted phenyl group.

9. A method of claim 8 wherein the phenyl group is substituted with a methyl, cyano, nitro, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methoxy, phenyloxy, benzyloxy, phenylaminooxy, phenylaminocarbonyl, methyoxycarbonyl, methylaminocarbonyl, dimethylamino, dimethylaminocarbonyl, or hydroxylaminocarbonyl group.

10. A method of claim 6, wherein $R_4$ of the structure is a hydrogen atom and $R_3$ is a cyclohexyl group.

11. A method of claim 6, wherein $R_4$ of the structure is a hydrogen atom and $R_3$ is a methyoxy group.

12. A method of claim 6, wherein $R_3$ and Rbond together to form a piperidine group.

13. A method of claim 6, wherein $R_4$ of the structure is a hydrogen atom and $R_3$ is a hydroxyl group.

14. A method of claim 6, wherein $R_4$ of the structure is a hydrogen atom and $R_3$ is a benzyloxy group.

15. A method of claim 6, wherein $R_4$ of the structure is a hydrogen atom and $R_3$ is a $\delta$-pyridine group.

16. A method of claim 6, wherein $R_4$ of the structure is a hydrogen atom and $R_3$ is a $\beta$-pyridine group.

17. A method of claim 6, wherein $R_4$ of the structure is a hydrogen atom and $R_3$ is a $\alpha$-pyridine group.

18. A method of claim 6, wherein $R_3$ and $R_4$ are both methyl groups.

19. A method of claim 6, wherein $R_4$ of the structure is a methyl group and $R_3$ is a phenyl group.

* * * * *